(12) United States Patent
Schimmel

(10) Patent No.: US 7,276,335 B1
(45) Date of Patent: Oct. 2, 2007

(54) DESIGNING COMPOUNDS SPECIFICALLY INHIBITING RIBONUCLEIC ACID FUNCTION

(75) Inventor: Paul R. Schimmel, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 08/249,689

(22) Filed: May 26, 1994

Related U.S. Application Data

(63) Continuation of application No. 08/129,787, filed on Sep. 29, 1993, now abandoned.

(51) Int. Cl.
C12Q 1/68 (2006.01)
C12N 15/11 (2006.01)
G06G 7/60 (2006.01)

(52) U.S. Cl. .......................... 435/6; 536/24.1; 703/11

(58) Field of Classification Search ............... 435/6, 435/320.1; 536/27, 23.1; 436/501; 935/77, 935/78
See application file for complete search history.

(56) References Cited

U.S. PATENT DOCUMENTS 4,464,359 A * 8/1984 Suhadolnik et al. ........ 424/180
4,757,055 A * 7/1988 Miller et al. ................. 514/44
4,898,818 A * 2/1990 Nakai et al. ............... 435/69.1
4,924,624 A * 5/1990 Suhadolnik et al. ........... 47/58

OTHER PUBLICATIONS

Jeong, K.S. and Rebek, J. Jr. J. Amer. Chem. Soc. 110 3327-3328 (1998) "Molecular Recognition . . . Hydrogen Bonding and Aromatic . . . ".*
Rebek, J. Jr. et al., J Amer. Chem. Soc. 109 5033-5035 (1987) "Molecular Recognition: Hydrogen bonding and stacking interactions . . . ".*
Wilson, W.D. et al., Biochemistry 32 4098-4104 (1993) "The Search for Structure-Specific Nuleic Acid-Interative drugs . . . ".*
Yamada, T. et al., Nucleic Acids Research 8 5767-5777 (1980) "The Translocation Inhibitor Tuberactinomycin binds to nucleic . . . ".*
Wank, W. et al., J. Mol. Biol. 236 1001-1010 (1994) "Peptide Anibiotics of the Tuberactinomycin family as inhibitors . . . ".*
Askew, B., et al., J. Amer. Chem. Soc. 111 1082-190 (1989) "Molecular Recognition With Convengent Functional Groups . . . ".*
von der Haar, Von Friedrich et al. Angew Chem. 93:250-256 (1981).
Brierley, Ian, et al. Cell 57:537-547 (1989).
Mei, Houng-Yau, et al. Proc. Natl. Acad. Sci. 86:9727-9731 (1989).
Yokoyama, Masayuki, et al. Chemical Abstracts 109: 79550 No. 79541c (1988).
Itai, Akiki, Chemical Abstracts 108:398 No. 62280y (1988).
Badger, John, et al. J. Mol. Biol. 207:163-174 (1980).
McKinlay, et al. Ann. Rev. Pharmacol. Toxicol. 29:111-122 (1989).
Perry, N.C., et al. in QSAR: Quantitative Structure Activity Relationships in Drug Design, Alan R. Liss, Inc. pp. 189-193 (1989).
Ripka, William New Scientist 54-56 (Jun. 16, 1988).
Rouvinen, Juba, et al. Acta Pharmaceutica Fennica 97:159-166 (1988).
Williams, et al. J. Am. Chem. Soc. 111:1090-1094 (1989).
Benzing, T., et al. Science 242:266-268 (1988).
Goodford, Peter Chem. Abstracts 111 No. 126283y (1989).
Weber, I., Proteins: Structure, Function, and Genetics 7:172-184 (1990).
Malim, M., et al. Cell 60:675-683 (1990).
Schimmel, Paul Cell 58:9-12 (1989).
Endo, Yaeta, et al. The Journal of Biological Chemistry 265:2216-2222 (1990).
Von der Haar, Friedrich et al. Chemical Abstracts 94:346 No. 197448x (1981).
Park, Soon Jae, et al. The Journal of Biological Chemistry 263:16527-16530.
Roberts, Stanley M., ed. Molecular Recognition: Chemical and Biochemical Problems, CRC Press, 1989.
Rebek, Jr., Julius, Science 235:1478-1484 (1987).
Rebek, Jr., J., et al. J. Am. Chem. Soc. 109:2426-2431 (1987).
Rebek, Jr., Julius, et al. J. Am. Chem. Soc. 107:6736-6738 1985).
Askew, Ben, et al. J. Am. Chem. Soc. 111:1082-1090 (1989).
Lewis, R. A. , et al. Proc. R. Soc. Lond. 236:125-140 (1989).
Lewis, R.A., et al. Proc. R. Soc. Lond. 236 :141-162 (1989).
Dreher, T.W., et al. J. Mol. Biol. 201:41-55 (1988).
Jacks, Tyler, et al. Cell 55:447-458 (1988).
Pleij, Cornelis, W.A., et al. Nucleic Acids Research 13:1717-1731.
Haenni, Anne-Lise, et al. Progress in Nucleic Acid Research and Molecular Biology 27:85-105.
Robertus, J.D., et al. Nature 250:546-551 (1974).
Kim, S.H., et al. Science 185:435-440 (1974).

(Continued)

Primary Examiner—John S Brusca
(74) Attorney, Agent, or Firm—Pabst Patent Group LLP

(57) ABSTRACT

A method for designing compounds specifically targeting RNA sequences, based on the discovery of short, specific sequences within RNA that are critical to function, using modeling of the compound to effect binding to the nucleotide sequences in the RNA in combination with secondary and/or tertiary structure associated with the minor groove of the RNA in the region of the critical sequences. In the preferred method, computer modeling is used along with analysis of the targeted RNA sequence to design molecules binding to the targeted RNA by covalent or hydrogen binding. Appropriate molecules are synthesized using known methodology that have the required structure and chemical characteristics to specifically bind the critical region of the RNA and thereby inhibit the function of the RNA. Molecules known to bind to RNA can also be modified using this method to increase specificity, and thereby decrease toxicity.

13 Claims, 5 Drawing Sheets

OTHER PUBLICATIONS

Hou, Ya-Ming, et al. *Nature* 333:140-145 (1988).
Park, Soon Jae, et al. *Biochemistry* 28:2740-2746 (1989).
Francklyn, Christopher, et al. *Nature* 337:478-481 (1989).
Hou, Ya-Ming, et al. *Biochemistry* 28:6800-6804 (1989).
Schimmel, Paul *Biochemistry* 28:2747-2759 (1989).
Hou, Ya-Ming, et al. *Trends in Biochemical Sciences* 14:233-237 (1989).
Weber, I.T., et al. *Science* 243:928-931 (1989).
Jones, T.Alwyn, et al. *The EMBO Journal* 5:819-822 (1986).
Shi, Jian-Ping, et al. *Science* 29:3621 (1990).

* cited by examiner

DESIGNING COMPOUNDS SPECIFICALLY INHIBITING RIBONUCLEIC ACID FUNCTION

This is a continuation of application Ser. No. 08/129,787 filed on Sep. 29, 1993, now abandoned which invention pertains generally to compounds and to the design of these compounds targeted to bind to ribonucleic acid; and, more particularly, to compounds that bind specifically to certain nucleotide base pairs in combination with elements of the secondary structure of the minor groove of ribonucleic acid molecules.

STATEMENT REGARDING FEDERALLY SPONSORED RESEARCH OR DEVELOPMENT

The government has certain rights in the invention by virtue of Grant No. 5R37GM15539-23 awarded by the National Institutes of Health to Paul R. Schimmel.

The Government has rights in this invention pursuant to grant Numbers GM15539 and GM23562 awarded by the National Institutes of Health.

BACKGROUND OF THE INVENTION

With few exceptions, ribonucleic acid (RNA) molecules are synthesized by the transcription of specific regions of deoxyribonucleic acid (DNA). The general function of RNA is as the intermediary of protein synthesis from DNA into the amino acid sequences of protein, although RNA has recently been discovered to have other functions, including enzymatic activity.

Three principal types of RNA exist in cells: messenger RNA, transfer RNA and ribosomal RNA. The messenger RNAs (mRNA) each contain enough information from the parent DNA molecule to direct the synthesis of one more proteins. Each has attachment sites for tRNAs and rRNA. The transfer RNAs (tRNA) each recognize a specific codon of three nucleotides in a strand of mRNA, the amino acid specified by the codon, and an attachment site on a ribosome. Each tRNA is specific for a particular amino acid and functions as an adaptor molecule in protein synthesis, supplying that amino acid to be added to the distinctive polypeptide chain. Subunits of ribosomal RNA (rRNA) form components of ribosomes, the "factories" where protein is synthesized. The subunits have attachment sites for mRNA and the polypeptide chain. The rRNAs regulate aminoacyl-tRNA binding, mRNA binding, and the binding of the initiation, elongation, and termination factors; peptide bond formation; and translocation, as reviewed by Endo, et al., *J. Biol. Chem.* 265:2216 (1990).

The RNAs share a common overall structure, though each kind of RNA has a unique detailed substructure. Generally, RNA is a linear, single-stranded (with a few viral exceptions), repetitive polymer in which nucleotide subunits are covalently linked to each other in sequence. Each nucleotide subunit consists of a base linked to the ribose-phosphate of the polymeric backbone. The bases in RNA are adenine (A), uracil (U), guanine (G), and cytosine (C). The sequence of bases imparts specific function to each RNA molecule. Nucleotide bases from different parts of the same or different RNA molecules recognize and noncovalently bond with each other to form base pairs. Since RNAs generally are a single covalent strand, base pairing interactions are usually intrastranded, in contrast to the interstrand base pairing of DNA. These noncovalent bonds play a major part in determining the three-dimensional structure of each of the RNAs and the interaction of RNA molecules with each other and with other molecules. The 2' hydroxyl group also influences the chemical properties of RNA, imposing stereochemical constraints on the RNA structure, by restricting the ribose conformation in oligomeric RNA molecules to the C3'-endo conformation, in contrast to DNA, where the sugars freely interconvert between the C3'-endo and C2'-endo puckered conformations.

The RNA molecule forms a helix with major and minor grooves spiralling around the axis, as shown in FIG. 1A. Nucleotide bases are arranged near the center of the helix with the ribose phosphate backbone on the outside. The bases are planar, perpendicular to the axis, and stacked on one another. Because the helix is in the alpha form, bases and sequences of bases are most accessible from the minor groove, which is wider and more shallow than the major groove, as discussed by Arnott, et al., *J. Mol. Biol.* 27:525 (1967). DNA, in contrast, is found as either an A- or B-form helix, as shown in FIGS. 1A and 1B, respectively. The different types of helical structure present different molecular surfaces to the proteins with which they make sequence-specific contacts.

RNA molecules assume a greater variety of tertiary structures than do DNA molecules, because of the lack of a complementary second strand and because of the potential to form Watson-Crick intrastrand hydrogen bonds between complementary sequences which can be well separated from each other in the linear sequence. In addition, the juxtapositioning of distant bases in the sequence allows for tertiary base pairing schemes that typically are non-Watson-Crick, such as Hoogstein pairing. Consequently, in the absence of proteins, doubled stranded DNA rarely assumes the globular forms characteristic of transfer RNAs or ribosomal RNAs. The higher order DNA structures that are found in vivo, including those resulting from supercoiling and those associated with the folding of chromosomes, are dependent on topoisomerases and packaging proteins. Even so, the condensation of DNA in chromosomes results in a structure that is more rod-like than globular.

Transfer RNA is the most well characterized of the RNA molecules. One or more specific tRNAs exists for each of the twenty amino acids in cells. The tRNA molecule is a 70 to 80 nucleotide strand forming two helical regions. One helical region terminates in the anticodon loop, which base-pairs to a complementary triplet in an mRNA codon. The other helical region terminates in the amino acid acceptor helix, which recognizes and binds a specific amino acid. Base pairing, as shown by crystallographic analysis, accounts for the formation of a two-dimensional stem-loop structure similar to a cloverleaf, forming the secondary structure of the molecule. See, e.g., Holmquist, et al., *J. Molec. Biol.* 78:91 (1973). As tRNAs line up on the mRNA molecule, bringing their amino acids into juxtaposition, they enable conversion of sequences of nucleotides into the sequences of amino acids that form the polypeptide chains. Hou & Schimmel, *Nature* 333:140 (1988). This function of tRNA is essential for protein synthesis. A related function of the tRNA molecule is to activate and enable the amino acid to react with another amino acid to form the peptide bond necessary for linkage. This step is also essential for protein synthesis. During protein synthesis, "the success of decoding is crucially dependent on the accuracy of the mechanism that normally links each activated amino acid specifically to its corresponding tRNA molecules." Alberts, B., et al., *Molecular Biology of the Cell,* 2d ed., Garland Publishing, Inc., page 207 (1989).

The reaction in which a tRNA becomes linked to the one appropriate amino acid is catalyzed by an enzyme, aminoacyl-tRNA synthetase. Each of the twenty amino acids requires a different synthetase enzyme that recognizes it and attaches it to one of its set of cognate tRNA molecules.

Since RNA is critical to protein synthesis and the transfer of genetic information encoded in the deoxyribonucleic acid (DNA) of eukaryotic cells, bacteria, and viruses, it represents a potential mechanism by which all pathogenic agents can be inhibited. At this time, however, little progress has been made in identifying a means by which RNA can be inhibited specifically.

Drugs that are currently available act on specific biochemical pathways via interaction with a particular protein or cofactor, or by interference in general with nucleic acid synthesis or translation. Most chemotherapeutic agents act by the latter mechanism, where the most rapidly replicating cells (usually the cancer cells) are inhibited more than the slower growing cells. The compounds are toxic to all cells, however.

It is therefore an object of the present invention to provide methods to make compositions, and the products thereof, that specifically inhibit RNA.

It is another object of the present invention to provide methods for designing compounds specifically inhibiting RNA that have low toxicity to normal eukaryotic cells.

It is a further object of the present invention to provide methods for screening and administering such compounds for specific inhibition of RNA.

SUMMARY OF THE INVENTION

A method for designing compounds specifically targeting RNA sequences by modeling the compound to bind to crucial short nucleotide sequences in the RNA in combination with secondary and/or tertiary structure associated with the minor groove of the RNA is provided. In the preferred method, a critical sequence of the RNA is identified, then computer modeling is used in combination with analysis of the targeted RNA sequence to design molecules binding to the targeted RNA by covalent or hydrogen binding. Appropriate molecules specifically inhibiting the function of the targeted RNA are synthesized using known methodology that have the required secondary structure and chemical characteristics. Molecules known to bind to RNA can also be modified using this method to increase specificity, and thereby decrease toxicity.

Much of the design of these compounds, as well as the inhibitory effect of these compounds, is based on studies on the recognition of RNAs by proteins in combination with in vitro RNA synthesis. For example, studies have demonstrated that the G3:U70 base pair of tRNA$^{Ala}$ is critical for its function. By taking advantage of sequence differences around G3:U70 between the human tRNA$^{Ala}$ and that of a pathogenic organism, selective drug binding can be achieved and protein synthesis by the pathogenic organism inhibited. Another example involves the interaction between the RNA-dependent reverse transcriptase of retroviruses and the specific tRNA that acts as a primer for reverse transcriptase. The annealing of the primer tRNA to the primer binding site is the first step in initiation of cDNA synthesis by reverse transcriptase, and thus represents a potential target for the arrest of viral multiplication. This can also be used as an assay for testing inhibitors of the binding reaction, for example, using glycerol gradient centrifugation to detect the presence of a complex between HIV reverse transcriptase and primer lysine tRNA.

Examples demonstrate the targeting of compounds to viral RNA which inhibit viral infection and/or replication, synthesis of compounds inhibiting viral reverse transcriptase, targeting of compounds to bacterial but not eukaryotic tRNA molecules to inhibit bacterial replication, and modification of compounds inhibiting rRNA to impart greater specificity and thereby decrease toxicity to normal cells.

DETAILED DESCRIPTION OF THE INVENTION

The method of the present invention depends on an understanding of the primary, secondary and tertiary structure of RNA and the determination of short nucleotide sequences essential for functioning of the RNA, particularly specialized RNA such as tRNA and rRNA. Compounds must bind to the targeted RNA with specificity, as determined by the secondary and/or tertiary structure and bonding with associated nucleotides, and effectively, by blocking access to the critical nucleotides required for function of the RNA.

Targeted RNA Molecules.

RNA molecules that can be inhibited include mRNA, tRNA, rRNA, and viral RNA. Both single strand and double strand RNA can be bound and therefore inhibited. Inhibition, as used herein, refers to a decrease in the RNA's function, where function may be transcription, translation, attachment of amino acids, activation of subsequent amino acids as required to form peptides, binding of initiation, elongation and termination factors, peptide bond formation, and translocation.

Proteins that participate in gene regulation, DNA synthesis, and other processes make the majority of their sequence specific contacts with B-form DNA through major groove interactions. Because the deep groove is too narrow for a protein in the form of an alpha-helix to make direct sequence-specific contact, the primary basis for sequence discrimination in RNA is usually the minor groove. Based on the three-dimensional structure of yeast tRNA$^{Phe}$, it has been proposed by Rich and Schimmel, *Nucl. Acids Res.* 4:1649 (1977, that sequence-specific recognition of the tRNA by aminoacyl tRNA synthetases occurs mainly through contacts along the inside surface of the tRNA "L" shape, where the minor groove is available and where the anticodon is located. Recognition and interaction with determinants may occur through hydrogen bonds to either the minor groove exocyclic amino or keto groups, or to the unpaired bases themselves.

Characterization of the Primary, Secondary and Tertiary Structure of the Targeted RNA.

Each RNA is characterized by its primary, secondary, and tertiary structure. Until recently, little has been known about specific RNA sequence and structure. Moreover, there has been a methodological problem in obtaining sufficient quantities of nucleic acid for testing model RNAs for recognition by new compounds. Large scale in vitro and chemical syntheses of RNA is now possible, allowing analysis by x-ray crystallography and other analytical methods. A number of interactive computer graphics programs are also available, which can be used for analysis of secondary and tertiary structure of the RNA. Both of these techniques can be used to predict new and improved molecular compounds that will bind specifically to selected sites on the RNA molecules.

Figures 1A, 1B:
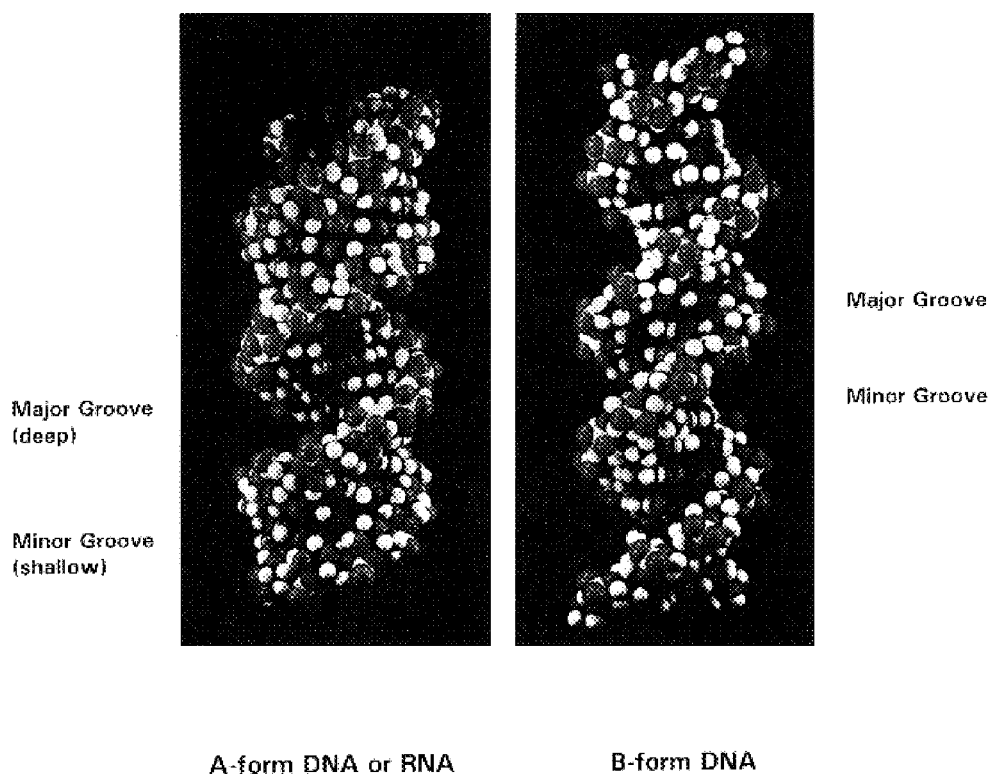
FIGS. 1A and 1B are prospective views of the A-form of DNA or RNA (FIG. 1A) and the B-form of DNA (FIG. 1B), showing the major and minor grooves, and three dimensional structure that can be specifically targeted according to the method of the present invention.
Figure 2A:
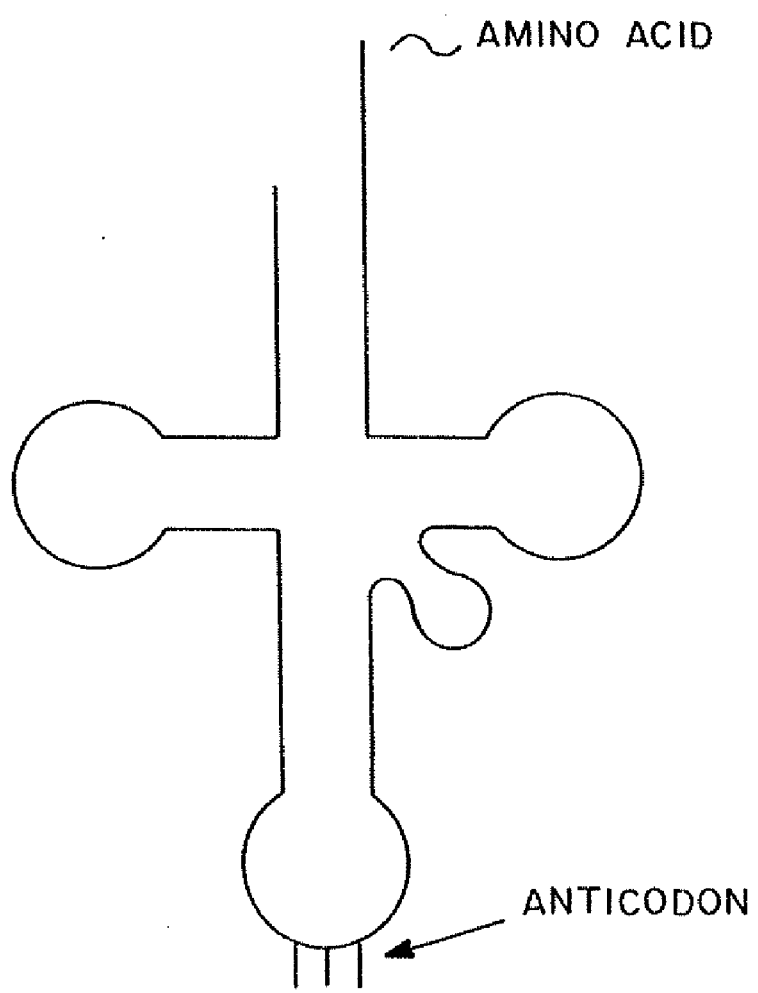
FIGS. 2A and 2B are a schematic (FIG. 2A) and a prospective view based on computer modeling (FIG. 2B) of a tRNA.
Figure 2B:
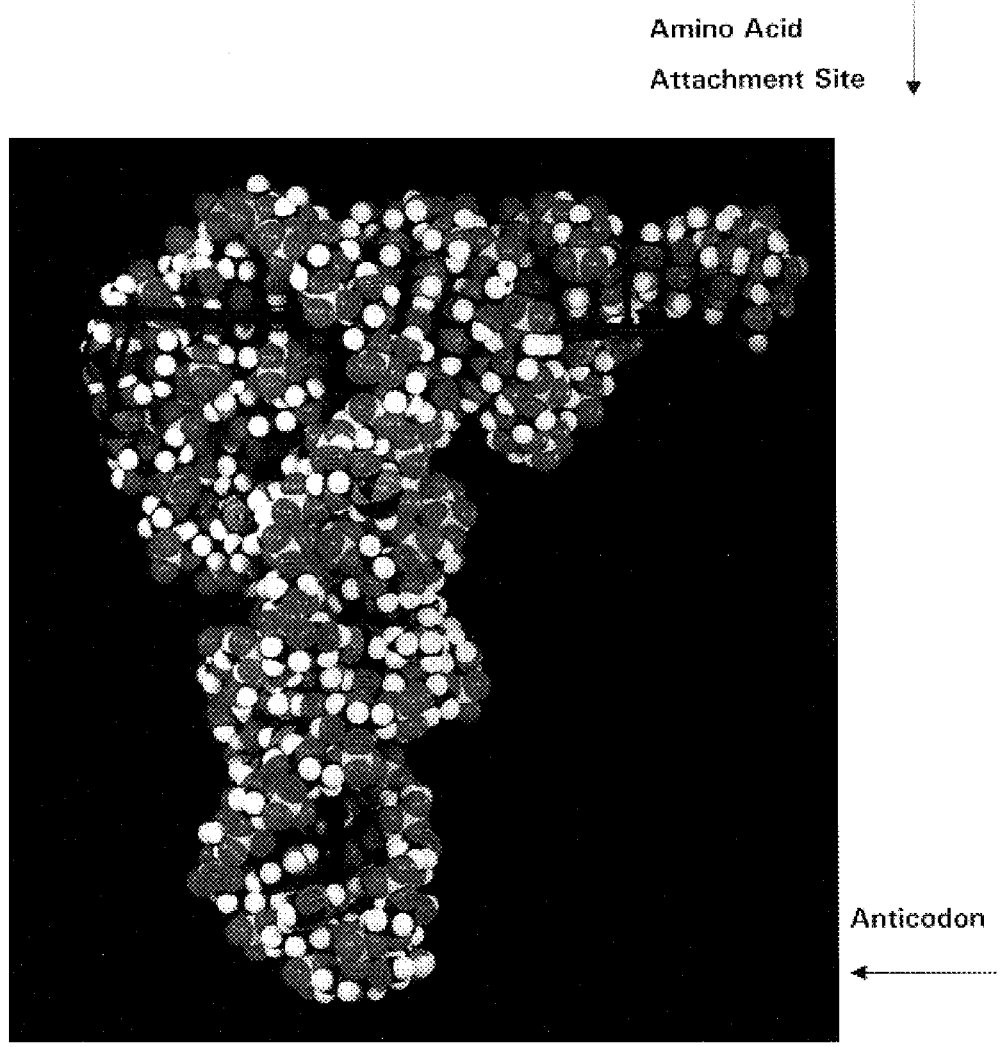

X-ray diffraction analyses have established that virtually all tRNA molecules exist as hydrogen-bonded cloverleaf secondary structures, with tertiary structure formed by additional folding, as depicted schematically in FIG. 2A and by computer modeling in FIG. 2B. High resolution, three-dimensional X-ray structures are available for four tRNAs, showing precise geometries of helical domains and confirming that the stem-loop is precisely folded into an L-shaped three-dimensional conformation, with two helices and major and minor grooves. Pleij, et al., *Nucleic Acids Research* 13(5), 1717-1731 (1985), reviews the tertiary interaction involving hairpin or interior loops of RNA, and other tertiary structures, and their impact on ribosome function, RNA splicing and recognition of tRNA-like structures.

The amino acid acceptor regions of many viral RNAs have also been sequenced. The secondary structures of viral RNAs probably are not in the form of the typical cloverleaf tRNA. However, the different primary and secondary structures of tRNAs and certain viral RNAs can be recognized efficiently by the same tRNA-specific enzymes, as reviewed by Haenni, et al., *Progress in Nucleic Acid Research & Molecular Biology* 27:85 (1982). For example, evidence indicates that viral RNAs of high molecular weight and eukaryotic tRNAs similarly recognize aminoacyl-tRNA synthetases. These data support the conclusion that the tertiary, rather than the primary and cloverleaf folding, determines recognition. For example, the brome mosaic plant virus has an RNA that can be specifically tyrosylated by tyrosyl-tRNA synthetases; the core region necessary for aminoacylation has been identified by Dreher and Hall, *J. Molec. Biol.* 210:41-55 (1988).

Characterization of Critical Sequences within the Targeted RNA Molecule.

Critical sequences of the targeted RNA molecule are determined using a method such as substitutional mutation and comparison of function of the mutated RNA with the original RNA; or base substitution in tRNA and determination of which amino acid is now recognized by the tRNA; the critical sequences may also affect, or be determined by, secondary and tertiary structure of the RNA molecule.

In the first method, substitution mutations are made in the RNA and the function of the mutated RNA compared with that of the original molecule. For example, nucleotide bases in the aminoacyl acceptor region of tRNA can be substituted and the resulting RNA tested to see if (1) an amino acid is attached and (2) if so, which one. The minimum number of nucleotide substitutions (sequence changes) that are required to convert a tRNA from one amino acid identity to another can be determined in this manner.

To practice this method, the RNA molecule is obtained either by in vitro transcription using bacteriophages that encode and synthesize polymerases, such as SP6 and T7, both of which are commercially available, by chemical synthesis, or by isolation from cells that produce the RNA.

A useful approach for elucidating and testing models for recognition is by investigation of substitution mutations of both the protein and of the nucleic acid. For RNA, one obstacle to this approach has been the difficulty in freely generating and isolating mutant and wild-type RNA species from whole cells in quantities that are sufficient for quantitative studies.

In Vitro Synthesis of RNA.

A number of advances in the field of in vitro RNA synthesis have greatly facilitated the generation of sequence and length variants of different RNAs. The in vitro enzymatic synthesis of RNA was originally beset by numerous technical impediments. Initially, transcripts were obtained by use of purified RNA polymerase from *E. coli*, which has three different subunits in the core enzyme ($\alpha$, $\beta$, $\beta'$) and a separate one for specific initiation ($\delta$). Each of these subunits must be cloned for optimal use of this system. Frequently, reactions carried out using this system were characterized by premature termination and the addition of non-template encoded polyuridine tracts to the ends of products. In later work, eukaryotic whole cell or nuclear extracts were used that either contained or were supplemented with RNA polymerases and other accessory factors. The runoff transcripts obtained from these extracts suffered from some combination of poor yields, incorrect initiation, and premature termination.

These technical barriers have been overcome through the use of transcription systems based on the bacteriophages SP6 and T7, which each encode RNA polymerases that are single polypeptide chains. The SP6 system was originally characterized by Butler and Chamberlin, *J. Biol. Chem.* 257, 5772-5778 (1982), and then used by Melton, et al., *Nucleic Acids Res.* 12, 7035-7056 (1984), to produce RNA probes of eukaryotic genes. These in vitro synthesized RNAs are superior to nick-translated DNA probes in their ease of synthesis and in their high specific activity. They also are useful for elaborating details about the mechanisms of RNA processing and for providing an efficient means to program in vitro translation.

The T7 RNA polymerase system was first characterized by Studier and co-workers, *J. Mol. Biol.* 153, 527-544 (1981) and *Proc. Natl. Acad. Sci. USA* 81, 2035-2039 (1984). This single subunit enzyme has a molecular weight of 92 kilodaltons (kDa), and has been cloned and over-expressed in bacteria to aid in its purification. T7 polymerase is highly specific for a 23 base pair promoter sequence that is repeated seventeen times in the T7 genome, but which has not been found in *E. coli* or other host DNAs. The viral promoter elements that are required for efficient transcription initiation have been incorporated into high copy vectors with multiple cloning sites for transcription templates, as reported by Rosenberg, et al., *Gene* 56, 125-135 (1987).

In both the T7 and the SP6 systems, a simple reaction of a few components is sufficient to obtain efficient in vitro synthesis, as described by Milligan, et al., *Nucleic Acids Res.* 15, 8783-8798 (1987). The T7 system is presently favored because of the greater number of initiations (greater than 100 versus less than 10) obtainable per template molecule as compared to the SP6 polymerase. The T7 RNA polymerase can initiate transcription from a promoter which is as small as eighteen base pairs. The transcribed sequence can be single stranded, so that transcripts up to tRNA length, about 80 nucleotides, can be obtained from a template which has a double stranded promoter and single stranded coding sequence. This system has limitations, because T7 RNA polymerase prefers to initiate transcription at a G and, in addition, the sequence of the transcript from +1 to +6 has a marked effect on the yield of product.

Chemical Synthesis of RNA.

A complementary approach to the in vitro synthesis of RNA is the use of chemical synthesis, as described by Cedergren, et al., *Biochem. Cell. Biol.* 65, 677-729 (1987). Early workers in this field were stymied by a number of problems, especially the reactivity of the 2' hydroxyl and the relative ease of hydrolysis of RNA under mild alkaline conditions. In order to bring chemical RNA synthesis up to the level of simplicity and repeatability of chemical DNA synthesis, an effective protecting group for the 2' hydroxyl is required, as described by Caruthers, et al., *Chem. Scr.* 26, 25-30 (1986). Usman, et al., and others, *J. Am. Chem. Soc.* 109, 7845-7854 (1987) and *Biochemistry* 28, 2422-2435 (1989), demonstrated the feasibility of the in vitro synthesis of long ribonucleotides by development of 3'-O-phosphoroamidites that were protected at the 2' position with a tert-butyldimethylsilyl (TBDMS) moiety. In conjunction with controlled pore glass supports, the use of these monomers has permitted the complete chemical synthesis of a 77-nucleotide RNA sequence corresponding to tRNA$^{Met}$, as reported by Ogilview, et al., *Proc. Natl. Acad. Sci. USA* 85, 5764-5768 (1988). When tested with a purified preparation of methionine tRNA synthetase, the chemically synthesized tRNA had a methionine acceptance of 11% of that of the native tRNA. The chemical approach provides methods for introducing unusual bases into RNA, mixed intra-chain RNA-DNA hybrid molecules, and other RNAs not available through enzymatic means.

Proteins which Interact with tRNAs and tRNA-Like Structures.

As discussed above, the aminoacyl tRNA synthetases are an ancient class of enzymes that catalyze the two-step aminoacylation reaction. There is one enzyme for each amino acid, and that enzyme charges all isoacceptors of its cognate tRNA species. In the first step of the reaction, the amino acid is activated by condensation with ATP to produce a bound adenylate; subsequently, the activated amino acid is transferred to the 3' end of the cognate tRNA. The esterified tRNA forms a complex with elongation factor Tu, which delivers the charged tRNA to the ribosome. Although all synthetases catalyze the same reaction, they are diverse with respect to sequence, length, and quaternary structure, as reviewed by Schimmel, *Ann. Rev. Biochem.* 56, 125-158 (1987).

When the first sequences of the tRNA molecules were obtained, the base pairing that gives rise to stems and loops suggested the two-dimensional cloverleaf structure that is now the conventional schematic representation of tRNAs. This was confirmed by extensive physical studies. A complete three-dimensional model of a tRNA, based on x-ray diffraction and crystallographic studies and defining the positions of all nucleotide residues, was first described for yeast phenylalanine tRNA (tRNA$_{Phe}$). Kim, et al., *Science* 185:435 (1974); see also Robertus, *Nature* 250:546 (1974). At the time of the elucidation of the first sequence, the function of conserved unpaired bases in the cloverleaf was unknown. The x-ray structure revealed the participation of conserved nucleotides, such as U8, A14, G15, G22, G46 and φ55, in unusual base-pairing schemes. These interactions feature triple base pairs, reverse Hoogsteen base pairs, and hydrogen bonds between bases and the sugar-phosphate backbone. Collectively, they establish the compact, L-shaped structure of tRNA, whereby the four helical stems are fused into two helices (the acceptor and TφC stems are stacked together, as is the D-stem with the anticodon stem) and the D- and TφC-loops are annealed together. The triple base pair between G22, C13, and G46 in tRNA$^{Phe}$ strengthens the interaction between the TφC and dihydrouridine loops, and provides greater resistance to thermal, chemical, and enzymatic degradation. Base pairs can also hydrogen bond with the free 2'-hydroxyl of ribose or, as in the ternary interaction between G18, φ55, and phosphate 58, with the phosphate oxygen from another portion of the backbone. The specificity of an aminoacyl-tRNA synthetase for its cognate tRNA molecule lies in the three-dimensional structures of the two molecules. The sequence elements that establish the recognition of one tRNA by the aminoacyl-tRNA synthetase has been reported by Schimmel, *Biochem.* 28:2747 (1989). The G3:U70 base pair in the amino acid acceptor helix is unique to tRNA$^{Ala}$ and is a major determinant in identifying alanine. Hou & Schimmel, *Nature* 333:140 (1988); Francklyn and Schimmel, *Nature* 333:478 (1989); Park et al., *Biochem* 28:2740 (1989); Hou and Schimmel, *Biochem.* 28:6800 (1989).

One structural feature demonstrated to be common to several synthetases is that sequences involved in adenylate synthesis are localized to the amino terminal part of the protein, while some of the sequences involved in tRNA binding are located in the carboxyl terminal half. The most conserved structure is the dinucleotide binding fold, an alternating arrangement of beta strands and alpha helices that contains the sequences responsible for adenylate synthesis.

The recognition problem has been investigated for a number of years by many different approaches, as reviewed by Schimmel, *Biochemistry* 28, 2727-2759 (1989) and *Ann. Rev. Biochem.* 56, 125-158 (1987), Normanly and Abelson, *Ann. Rev. Biochem.* 58, 1029-1049 (1989), Schulman and Abelson, *Science* 240, 1591 (1988), Yarus, *Cell* 55, 739-741 (1988), Schimmel and Soll, *Ann. Rev. Biochem.* 48, 601-648 (1979). An important distinction between this interaction and that between regulatory proteins and DNA is that synthetase discrimination between tRNAs can occur at a binding and at a catalytic step. Unlike the interaction of a repressor with a DNA operator, the tRNA-enzyme complex must dissociate quickly to maintain protein synthesis. Consequently, the interaction is not as tight as repressor-operator interactions, and this limits the extent to which recognition can be achieved at the binding step. Dissociation constants at pH 7.5 are in the range of 0.1 to 1.0 μM, which is at least four orders of magnitude weaker than a typical repressor-operator complex. The study of numerous cognate and non-cognate synthetase interactions has shown that, for some complexes, binding discrimination may only contribute a 100-fold preference for the correct tRNAs, while discrimination at the transition state of catalysis may be as high as 104.

In one of the earliest systems for studying tRNA recognition, variants of an *E. coli* supF amber suppressor (normally inserts tyrosine at UAG codons) were isolated that were aminoacylated with glutamine, Ozeki, et al., *Transfer RNA: Biological Aspects* (Soll, Abelson, Schimmel, eds) pp. 341-362 (Cold Spring Harbor Laboratory, Cold Spring Harbor, N.Y. 1980). Determination of the minimal sequence changes associated with mischarging identified several positions within the acceptor end of the tRNA. These mutations included A73→G, as well as substitutions for the G1:C72 base pair. The molecular basis of glutamine mischarging with these mutant tRNAs was obscure, as some of these changes did not bring the suppressor sequence into closer agreement with tRNA$^{Gln}$. In the absence of an understanding of the molecular basis of glutamine mischarging, it was not clear how this type of genetic selection could be applied to other tRNAs. With the tRNA$^{Gln}$-GlnRS co-crystal now in hand, the effect of these mutations on mischarging can be rationalized.

Anticodon Substitutions.

Abelson, et al., *Proc. Natl. Acad. Sci. USA* 83, 6548-6552 (1986), synthesized a set of tRNA genes coding for amber-suppressing tRNAs (CUA anticodon), with the object of defining the minimal set of nucleotide substitutions that are required to convert a tRNA from one amino acid identity to another. So far, introduction of the CUA amber anticodon into 11 of 20 tRNAs does not change the amino acid attached in vivo, as reported by Normanly and Abelson, *Ann. Rev. Biochem.* 58, 1029-1049 (1989). This set includes: Ala, Gly, Cys, Phe, ProH, HisA, Lys, Ser, Gln, Tyr, and Leu. The remaining tRNAs can be divided into two groups; the first, which includes tRNAs for Ile, Gly, Met, Glu, and Trp, are all mischarged with glutamine. The second group includes those CUA-anticodon tRNAs which are mis-charged with lysine tRNA synthetase (Ile, Arg, Met (m), Asp, Thr, and Val). For those tRNAs that are mischarged when their anticodons are substituted, one or more bases in the anticodon may be a recognition determinant for the cognate enzyme. Additionally or alternatively, it may be a determinant for the glutamine or lysine tRNA synthetases.

"Transplantation Assay".

Those tRNAs unaffected by anticodon changes can be studied through an in vivo "transplantation assay", as devised by Normanly, et al., *Nature* 321, 213-219 (1986). In this method, base substitutions are introduced into an amber suppressing tRNA gene, which is then transformed into an *E. coli* strain that also carries a plasmid with a reporter gene that bears an amber (UAG) mutation. If the amber suppressor is functional, the gene product from the reporter gene (typically dihydrofolate reductase) is sequenced to determine the identity of the amino acid that has been inserted at the amber codon. By this method, introduction of twelve nucleotides that are common to a set of serine tRNAs into a leucine tRNA isoacceptor was sufficient to confer some serine acceptance in vivo. Since then this approach has been extended to the study of tRNAAla, tRNAPhe, and tRNA$^{Arg}$.

Amber suppression is a valuable method for studying how the introduction of nucleotide substitutions into a tRNA sequence affect the amino acid identity of the tRNA. It is restricted, however, to those isoacceptors whose amino acid identities are preserved in the presence of a CUA anticodon. Another problem is that some variants do not accumulate to reasonable intracellular levels, owing to the effect of the nucleotide changes on stability and/or recognition by the processing system. Still another drawback to this approach is that the identity of a tRNA is influenced by competitive reactions between synthetases. Some tRNA variants can act as substrates in vivo for more than one aminoacyl tRNA synthetase. Consequently, altering the levels of synthetases by varying their relative gene dosages will change the amino acid acceptor identity of any "dual identity" tRNA. This phenomenon has been analytically treated by calculations that are based on kinetic parameters for aminoacylation in vitro with alanine and tyrosine of a tRNA$^{Tyr}$ variant which encodes the major determinant for alanine identity, and is thus charged by tyrosine and alanine. The identity of a tRNA may therefore represent the outcome of many potentially competing interactions between a tRNA and the whole set of cognate and non-cognate synthetases in the cell. For these reasons, examining the interaction of a tRNA with its cognate synthetase in the absence of competing interactions provides information that is obscured by amber suppression.

Since amber suppression can, in some cases, occur with substrate variants which charge poorly or not at all in vitro, suppression can be insensitive to large variations in the efficiency of aminoacylation and cannot be used to make an analytical estimate of the contribution of specific nucleotides to recognition. Studies carried out in vitro circumvent the problems associated with the excess sensitivity of amber suppression, which is influenced by factors in addition to aminoacylation.

The sequence elements that establish the recognition of several tRNAs by the aminoacyl-tRNA synthetase have been reported by Schimmel, *Biochem.* 28:2747 (1989). These sequence elements were determined by constructing synthetic minihelices corresponding to regions of the targeted RNA and comparing their activity with that of the intact molecule.

As reported by Francklyn and Schimmel, *Nature* 337:478 (1989), a synthetic minihelix that reproduces the base pairs of the tRNA$^{Ala}$ amino acid acceptor stem and includes the G3:U70 base pair can be aminoacylated at a rate similar to that of tRNA$^{Ala}$, suggesting that this is the primary interaction site between the aminoacyl-tRNA synthetase and the tRNA molecule. Aminoacylation efficiency is markedly improved when the minihelix includes A73. In contrast, minihelices with substitutions at the 3:70 sites are not aminoacylated by alanine tRNA synthetase.

Nucleotide sequence variants of amber-suppressing derivative of *E. coli* tRNA$^{Ala}$ have also been screened, focusing on variations on the inside of the L-shaped structure. Two base pairs were found to confer alanine tRNA identity, as reported by Hou & Schimmel, *Nature* 333:140 (1988).

Evidence indicates that the enzyme finds access to the base pairs in the RNA helix through the minor groove.

Further data supports the utility of this screening method. For example, *E. coli* supF amber suppressor anticodon was substituted in twenty tRNAs for their anticodons. Recognition of some amino acids by the tRNAs were changed. In another example, *E. coli* tRNA$^{Met}$ anticodons were substituted with other anticodons. The results showed that this anticodon is critical to recognition by methionine tRNA synthetase; other regions of sequence have secondary importance for specificity. When the valine anticodon was substituted in tRNA$^{Met}$ and the methionine anticodon in tRNA$^{Val}$, the tRNAs interacted with the opposite synthetase from the original. Similar results were obtained when the arginine anticodon was substituted.

In addition to altering the amino acid recognized by the tRNA, in studies using yeast tRNA$^{Phe}$, substituting bases in the anticodon decreased the rate of aminoacylation with the synthetase. Transplantation experiments, discussed below, defined the recognition sequence as consisting of only five bases.

Using an in vivo transplantation assay, twelve tRNA$^{Ser}$ nucleotides substituted in tRNA$_{Leu}$ conferred serine binding on the tRNA$^{Leu}$. Similar results were obtained with tRNA$^{Ala}$, tRNA$^{Phe}$, TRN$^{Arg}$.

Design of Compounds Targeted to RNA Sequence in Combination with Secondary Structure.

Extrapolated from Comparisons of Protein-Nucleic Acid Interactions.

Once it is understood that RNA has short, specific regions that are critical to its activity, compounds specifically inhibiting the RNA can be designed and synthesized using methodology derived from studies using DNA and DNA-protein interactions, in combination with an understanding of the differences in the chemical and physical composition of RNA as compared to DNA, and knowledge as to the specific region to be inactivated.

The binding of proteins to specific sites in double-stranded DNA is an integral part of gene regulation, DNA synthesis, repair, recombination, and cleavage. X-ray structures have been obtained for several protein-DNA complexes, all of which result from sequence-specific contacts with B-form DNA through major groove interactions. The chemical basis for the discrimination between different base pairs lies in the order of hydrogen bond acceptor and donor groups across the base pair that is accessible to a protein. In principle, this potential array of hydrogen bonds permits all four base pairs to be distinguished from each other on the basis of major groove interactions. In each protein-DNA complex, the conformation of the protein, sometimes in conjunction with bends or kinks in the DNA conformation, acts to position uniquely the specificity-determining polar side chains with respect to the major groove in an orientation that is idiosyncratic to the complex. The nature of the base pair recognized by any particular amino acid side chain will depend on local geometry.

As initially suggested by modeling studies, reported by Lewis, et al., *Cold Spring Harbor Symp. Quant. Biol.* 47, 435-440 (1983), based on the uncomplexed proteins and helix swapping experiments using repressors such as the lac repressor, reported by Wharton and Ptashne, *Cell* 38, 361-369 (1984), the repressors use a conserved α-helix-β-turn-α helix to contact DNA, with the second of the two helices lying directly in the major groove. Polar side chains in this structural unit make contact with major groove bases in the operator through a series of hydrogen bonds and, occasionally, through hydrophobic interactions. Variations on this basic theme are found. For example, in lambda repressor, the amide NH group of the side chain of Gln44 donates a hydrogen bond to ring N7 in an A:T pair, while the side chain carboxyl oxygen accepts a hydrogen bond from the exocyclic N6 of adenine. This bidentate interaction is further stabilized by a hydrogen bond from the amide group of Gln44 to the amide carboxyl of Gln33, while the amide amino group of Gln33 donates a hydrogen bond to the phosphate oxygen 5' to the A:T pair. Thus, amino acid-base pair contacts can be part of a network of specific hydrogen bonds. In the case of trp repressor, tightly bound water molecules are thought to provide specificity by bridging between groups that are not in direct contact. Hydrogen bonds from peptide amide groups to the phosphate backbone may help to maintain specificity by fixing the orientation of the helix-turn-helix with respect to the major groove. Often, subtle features of the DNA sequence influence the specificity of these protein-DNA interactions by modulating the DNA conformation, so as to create a molecular surface which is complementary to the protein, as discussed by Aggarwal, et al., *Science* 242, 899 (1988).

Like the repressors, Eco RI endonuclease also uses α-helices to make hydrogen bonds with the major grooves of its GAATTC recognition sequence, but the recognition helices do not assume a helix-turn-helix structure. The amino-terminal ends of the two recognition helices in each of the two subunits point into the major grooves bases of the inner tetranucleotide AATT. This places specificity-determining amino acid side chains in the proper orientation for base recognition: the carboxyl group of Glu144 receives hydrogen bonds from the successive N6 adenine exocyclic amino groups, while the Arg145 guanidinium donates two hydrogen bonds to the imidazole N7 nitrogens of the adenines located across the axis of symmetry. These "bridging" contacts, in which a single amino acid makes hydrogen bonds to functional groups on two successive base pairs, are unique to the Eco RI complex. The hydrogen bonds donated by each Arg200 guanidinium group to the O6 and N7 of the outer guanines, by contrast, are typical of the contacts made by the repressors.

Figure 3:
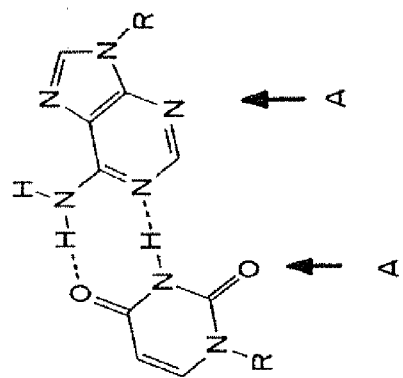
FIG. 3 is a schematic comparing the potential hydrogen bond donors and acceptors presented by G:C and A:T (or A:U) base pairs from the face of the minor groove than from the face of the major groove.

Given that there are limited restrictions on RNA shape and conformation, there are no simple symmetry considerations that might suggest how proteins recognize RNA sequences. However, the RNA 11 conformation of RNA helices imposes some limits on the potential interactions with protein side chains. In particular, the deep groove of this helical conformation is too narrow for protein structural motifs such as the α helix to make direct sequence-specific contact. Therefore, the primary basis for sequence discrimination in RNA is believed to be the minor groove. As shown in FIG. 3, there are fewer differences in the pattern of potential hydrogen bond donors and acceptors presented by G:C and A:T (or A:U) base pairs from the face of the minor groove than from the face of the major groove. Because both C and U have the 2-keto group as a potential hydrogen bond acceptor in the minor groove, discrimination between some of the base pairs may be based on the exocyclic 2-amino group of guanine. This expectation is fulfilled in the structure of the Gln-tRNA synthetase-tRNA$^{Gln}$ complex, reported by Woo, et al., *Nature* 286, 346-351 (1980).

The three-dimensional structures of transfer RNAs are closely similar. With some specific local features that are idiosyncratic to each tRNA, the molecule features two helical regions, one of which terminates in the amino acid acceptor end, while the other terminates in the anticodon. As a result, the structure of yeast tRNA$^{Phe}$ can be used as a model for interpreting results on the sequence-specific recognition of most tRNAs. After the yeast tRNA$^{Phe}$ structure became available, Rich and Schimmel, *Nucl. Acids Res.* 4, 1649-1665 (1977), considered photochemical cross-linking, tritium labeling, and nuclease digestion data on synthetase-tRNA complexes and proposed that recognition is mediated principally through contacts made along the inside surface of the tRNA "L". On this surface, both helical domains are potential sites for sequence-specific recognition through minor groove discrimination. In addition, at the inside of one end of the "L" the anticodon is a natural site for discrimination because the bases are unpaired, and because this sequence codes for the attached amino acid. On the outside of the L, an alternative region is the "variable pocket", which is formed by the interaction of the TφC and D loops, described by Ladner, et al., *Proc. Natl. Acad. Sci. USA* 72, 4414-4418 (1975) and McClain, et al., *Science* 241, 1804-1807 (1988). The nucleotides which comprise this patch, 16, 17, 59 and 60, are not conserved among tRNAs, and are not engaged in Watson-Crick base pairs. Accordingly, several different regions potentially can contribute recognition determinants, and possible interactions include hydrogen bonds to either the minor groove exocyclic amino or keto groups, or to the unpaired bases themselves.

In the co-crystal between *E. coli* tRNA$^{Gln}$ and the glutamine tRNA synthetase, the protein binds along the inside of the L-shaped structure. The anticodon and specific acceptor stem nucleotides are in contact with the synthetase. In the acceptor stem, the exocyclic 2-amino group of G2 forms hydrogen bonds to the backbone carboxyloxygen of Pro181 and to the backbone amide of Ile183. The latter interaction is bridged through a bound water molecule, in a fashion reminiscent of "indirect readout" first suggested in the trp repressor complex. A hydrogen bond to the exocyclic 2-amino group of G3 is made by the carboxyl of Asp235, which also hydrogen bonds to the previously mentioned water molecule.

A more complex feature is the interaction of the protein with the 3' end of the acceptor stem, and the conformational change by the nucleotides that are located in the 3' acceptor end. The U1:A72 base pair at the end of the acceptor stem is wedged open by the side chain of Leu136, which protrudes from a β-turn in the acceptor binding domain of the protein. The rate of charging of tRNA$^{Gln}$ variants is influenced by the propensity of this base pair to be melted out, as described by Seong, et al., *J. Biol. Chem.* 246, 6504-6508 (1989). The unpaired nucleotides (GCCA76) at the 3' acceptor end are folded back at a 90° angle with respect to the acceptor stem helix, such that the 3' end is buried deep within the dinucleotide binding fold, in close proximity to bound ATP and, presumably, the bound amino acid. The 2-amino group of G73 hydrogen bonds to the phosphate oxygen of the previous nucleotide. This interaction stabilizes the unusual conformation of the acceptor arm, and specifically depends on having a G at position 73. At present, it is clear that the recognition of tRNA$^{Gln}$ involves, at a minimum, contacts to the exocyclic amino groups in the minor groove and sequence-dependent conformation changes in the tRNA itself.

Comparison of Aminoacylation by Viral RNAs and tRNAs.

Some aminoacyl tRNA synthetases aminoacylate the 3' ends of certain genomic and subgenomic plant viral RNAs. This suggests a structural relationship between tRNAs and the 3' ends of these viral RNAs. Computer predictions of structure were tested experimentally with chemical probes by Dumas, et al., *J. Biomolec. Struc. & Cyn.* 4, 707-728 (1987), and led to the proposal of an RNA pseudoknot that enables a tRNA-like structure to form at the 3' end, by van Belkim, et al., *Nucl. Acids Res.* 16, 1931-1950 (1988).

In the RNA pseudoknot, bases in a hairpin loop form Watson-Crick pairs with bases that are located outside of the hairpin structure. Because less than 11 base pairs form with the loop, there is only partial revolution of one strand about the other, so that a true knot is avoided. In the pseudoknot described for turnip yellow mosaic virus, there is co-axial stacking of the two different helical stems of the pseudoknot. The stems are joined by two different connecting loops which cross the major and minor grooves, respectively. The pseudoknot structure is supported by the 2-D NMR studies of Puglisi, et al., *Nature* 331, 283-286 (1988), on short synthetic RNA fragments, where the stability of the pseudoknot has been shown to be sensitive to temperature and Mg2+ concentration.

Brome mosaic virus (BMV) RNA (aminoacylated by tyrosine) and turnip yellow mosaic virus (TYMV) RNA (aminoacylated with valine) are the most extensively studied plant viral RNAs. For BMV, a synthetic 135-nt fragment retains aminoacylation function. Dreher, et al., *Nature* 311, 171-175 (1984) explored the sequence requirements for aminoacylation with tyrosine and for viral replication by introducing mutations into the viral 3' end and at a putative AUA "anticodon" sequence. Those substitutions in which the CCA end was changed had abolished aminoacylation function, but retained at least partial replication function. The sequences at the AUA anticodon, by contrast, were not required for aminoacylation, but severely attenuated replication. The genetic separation of aminoacylation and replication functions in BMV RNA suggests that aminoacylation is not required for virus viability.

Dreher, et al., *Biochimie* 70, 1719-1727 (1988), synthesized a series of length variants of TYMV RNA in vitro and determined kinetic parameters for their aminoacylation by wheat germ valine tRNA synthetase. Although 83 3'-terminal nucleotides can be folded into a tRNA-like structure that can be aminocylated in vitro, sequences which lie upstream of this structure (between 82 and 159 from the 3' end) are required for a maximal rate and extent of aminoacylation. The decreased rate of aminoacylation of fragments shorter than 159 nucleotides is reflected predominantly in a decreased Vmax rather than Km, suggesting that the sequences 82-159 affect catalytic rather than binding steps. This is another demonstration of the significance of the transition state for catalysis for recognition by synthetases. Footprinting studies carried out on the fragments with purified synthetase suggest that the enzyme either contacts this region directly, or that this region is required for the correct conformation of the tRNA-like domain. Unlike the BMV RNA, the TYMV "anticodon" is an important determinant for aminocylation, as it is for *E. coli* tRNA$^{Val}$.

Studies Using RNase P, an Ribonucleoprotein Containing an RNA Molecule with Enzymatic Activity Cleaving Pre-tRNAs.

RNase P is required for maturation of the 5' ends of tRNA precursors. The enzyme has two different subunits in all organisms investigated so far. In *E. coli*, these consist of a 13.7 kDa protein component (C5), and a 377-nucleotide RNA component known as the M1 subunit, as reported by Altman, et al., *Trends Biol. Sci.* 11, 515-518 (1986). This nuclease distinguishes tRNA precursors from all other RNAs. Mutational analyses of precursor molecules showed that substitutions that disrupt the secondary or tertiary structure of the precursor inhibit the cleavage reaction, by Smith *Brookhaven Symp. Biol.* 20, 1902-1906 (1981) and McClain and Seidman, *Nature (London)* 257, 106-(1975). Thus, the enzyme is sensitive to the structure of the precursor. RNA synthesis of enzyme and substrate component has proved to be an effective way to approach recognition of tRNA precursors.

The essential role of RNA in the catalytic event was first demonstrated when cleavage of the precursor tRNA was shown to be dependent on both M1 RNA and C5 protein by Kole and Altman, *Biochemistry* 20, 1902-1906 (1981) and Reed, et al., *Cell* 30, 627-630 (1982). Subsequently, Guerrier-Takada, et al., *Cell* 35, 849-857 (1983) showed that the requirement for C5 could be overcome by raising the Mg2+ concentration from 10 to 60 mM. Kinetic parameters at 60 mM Mg2+ were determined for the holoenzyme reaction and for the reaction with M1 RNA alone. Under these conditions, C5 increased the velocity of the reaction by two-fold, but had no effect on the Km. The rnp A gene that codes for the C5 protein subunit is essential for viability in *E. coli*, so the operational Mg2+ concentration in vivo maybe closer to that (10 mM) used in the original assays. In vitro, it is possible to carry out complementation experiments utilizing the *E. coli* RNA and *B. subtilis* C5 protein. Thus, the protein may recognize features of the RNA structure which have been conserved during evolution.

The C5 protein and M1 RNA components of RNaseP have been cloned and over-expressed. Utilizing these reagents, Vioque, et al., *J. Mol. Biol.* 202, 835-848 (1988), measured a dissociation constant of $4 \times 10^{-10}$ M for the binding of M1 to C5. Footprint analysis showed protection of nucleotides between 82-86 and 170-270. A competition assay was used to examine the binding of synthetic truncated derivatives of M1 RNA to C5. A fragment formed of sequences from 94 to 272 effectively competed away binding to non-specific RNAs, while a fragment spanning either 1-168 or 164-272 did not.

A phylogenetic comparison of nine different sequences from two different eubacterial phyla established a "consensus" RNase P (Min 1) that contained only 263 nucleotides versus the 354 to 417 nucleotides of the parental structures, and incorporated stems, loops, and pseudoknot features that were conserved between all members of the collection, as reported by Waugh, et al., Science 244, 1569-1571 (1989). The Min 1 consensus also contained one of the regions implicated by footprinting, i.e., the sequences between 82 to 96 in E. coli M1 RNA. In vitro transcripts of the Min 1 structure processed a pre-tRN$^{Asp}$ substrate at a rate that was only five-fold slower than that of full length E. coli M1 RNA. The success of this design strategy is consistent with the belief that particular structural determinants of RNase P have been conserved through evolution.

The region from 86 to 92 in M1 has been further implicated by enzyme-substrate cross-linking studies by Guerrier-Takada, et al., Science 38, 219-224 (1984). Mixtures of M1 RNA and a pre-tRNA$^{Tyr}$ were irradiated with UV light at 300 or 254 nm, and then resolved on polyacrylamide gels to isolate the specific complexes. Reverse transcriptase was used to establish the points of crosslinking in both the enzyme and substrate. Reverse transcription terminated consistently at C93 in M1 RNA, indicating that C92 is cross-linked to the substrate. The cross-linking experiments also defined points of contact to the substrate. Efficient termination of reverse transcription (using a primer complementary to the 3' end of the tRNA precursor substrate) occurred at G-2, two nucleotides before the start of the mature tRNA. This indicated that C92 in M1 is cross-linked to "C-3" in the pre-tRNA. This is within three bases of the cleavage site in the pre-tRNA.

Deletion of C92 in M1 RNA raised Km by 100-fold and lowered kcat by 6-fold relative to wild type M1, in the absence of C5. However, the specific nucleotide at position 92 is not critical, because a U92 substitution mutant had nearly the same kinetic parameters for processing as wild type M1. Also, deletion of C92 can be partially overcome by the presence of the C5 subunit. Thus, N92 may influence the local conformation of the RNase P active site, but may be secondary to the influence of the C5 protein subunit.

In parallel with the work on the M1 RNA, in vitro RNA synthesis has also been used to investigate the substrate requirements for the reaction. Truncated version of E. coli tRNA$^{Phe}$ that retain the acceptor-TψC stem and loop are substrates for the enzyme, but the introduction of base substitutions at C74 (the 3' terminus is A76) eliminated cleavage. As described for alanine tRNA synthetase, RNase P recognizes a limited part of the overall tRNA structure. There is also evidence to suggest that RNase P recognizes the 3' CCA sequence of the precursor tRNA molecule, as reported by Guerrier-Takada, et al., Cell (1984). The precursor to E. coli tRNA$^{Tyr}$ is three nucleotides longer at the 3' end than the mature species, such that the sequence is CCAUCAOH. Cleavage of this substrate in vitro with M1 RNA or the RNase P holoenzyme reveals that the turnover number for the reaction with M1 RNA alone is greatly reduced in the absence of the CCA sequence. The wild type M1 RNA will correctly cleave a pre-tRNA$^{Tyr}$ which lacks the 3' terminal CCAUCA, although at a slower rate than for the wild type precursor. A mutant RNase P with a deletion of C92 also cleaves the mutant precursor, but does so at a site that is 4 to 6 bases upstream of the wild type cleavage site. Reverse transcription of a photo-crosslinked complex between the mutant M1 RNA and the mutant pre-tRNA$^{Tyr}$ gave strong termination at G1 in pre-tRNA. Since high concentrations of exogenous CCA trinucleotide inhibit the reaction of a substrate that contains the CCA group, but stimulates the processing of a substrate that lacks the trinucleotide, RNase P may have two separate binding sites for the pre-tRNA, one associated with the eventual site of cleavage, and one for the CCA end.

In the case of synthetic tRNAs, one drawback is that the transcripts are unmodified. The lysidine in the E. coli tRNA$^{Ile2}$ isoacceptor is one example of a modified base shown to be essential for aminoacylation with isoleucine. However, unmodified transcripts have been used to purify and characterize several nucleotide modification enzymes, including pseudouridine synthase from S. cerivisiae, and guanine methyltransferase from Xenopus oocytes. Microinjection of in vitro transcripts into Xenopus oocytes can be used to produce modified tRNAs in vivo. As more of the genes coding for the tRNA modification enzymes are cloned and their gene products characterized, tRNA transcripts produced in vitro can be treated with these enzymes to study the effects of modifications on molecular recognition.

The methods described generally above for the determination of critical regions of targeted RNA, the associated primary, secondary and tertiary structure, and design of molecules interactive with these regions to inhibit the function of the targeted RNA will be further understood with reference to the following non-limiting examples.

EXAMPLE 1

Determination of the Recognition Determinants for the E. coli tRNA$_i^{Met}$

Schulman and co-workers have studied the recognition determinants for the E. coli tRNA$_i^{Met}$ by several in vitro techniques. Originally, bisulfate-induced conversion of C34→U (first position of anticodon) in tRNA$^{fMet}$ was shown to have a strong negative effect on aminoacylation. This observation was followed by use of in vitro RNA synthesis to incorporate all four possible NAU anticodons into tRNA$_i^{Met}$. The substitution was performed by limited digestion of the tRNA with RNase A to remove the native anticodon, followed by the insertion (by ligation) of the substituted trinucleotides. Later, substitutions were made at each of the three positions. These experiments showed that substitutions at C34 decrease aminoacylation with purified methionine tRNA synthetase by four to five orders of magnitude, while substitutions of A35 and U36 were slightly less detrimental. A similar experiment showed that changing the fourth base from the 3' end of the tRNA (the "discriminator base") had no effect on aminoacylation of tRNA$_i^{Met}$.

The role of the anticodon in determining tRNA$^{Met}$ identity was further investigated through the in vitro synthesis of anticodon variants of tRNA$^{Met}$, tRNA$^{Trp}$, and tRNA$^{Val}$. Introduction of the methionine CAU anticodon into tRNA$^{Val}$ and tRNA$^{Trp}$ conferred aminocylation with methionine at a rate (expressed as relative V/Km) that was within 10% of that of tRNA$^{Met}$. This suggests that methionine tRNA synthetase recognizes the anticodon of tRNA$^{Met}$, and that other regions of the sequence are secondary for specificity. In vitro tRNA synthesis was used to show that a reciprocal exchange of the valine and methionine anticodons into the respective tRNAs makes them excellent substrates for the reciprocal synthetase. More recently, the CCG anticodon and A20 of tRNA$^{Arg}$ were introduced into tRNA$^{Met}$, and the latter was transformed into an excellent substrate for arginine tRNA synthetase.

With the availability of X-ray structural data for yeast tRNA$^{Phe}$, the effect of particular nucleotide substitutions on structure-function can be more accurately modeled than in the case of tRNAs for which no crystal structure yet exists. As in the case of tRNA$^{Met}$, the role of the anticodon in tRNA$^{Phe}$ recognition was initially investigated by use of RNase A digestion and T4 RNA ligase to make anticodon substitutions. Using this method, it was reported that substitution of any one of the three GAA anticodon nucleotides resulted in a 3 to 12 fold decrease in aminoacylation by purified yeast phenylalanine tRNA synthetase. However, introduction of the GAA anticodon into yeast tRNA$^{Tyr}$ gave a substrate which was only poorly aminoacylated with phenylalanine, suggesting that yeast Phe tRNA synthetase is sensitive to other sites.

A more complete characterization of yeast tRNA$^{Phe}$ was carried out by Samson, et al., *Proc. Natl. Acad. Sci. USA* 85, 1033-1037 (1988) and *Science* 243, 1363-1366 (1989), utilizing the T7 system. They provided the first example of an in vitro tRNA transcript that could be quantitatively aminoacylated in vitro. This result showed that modified bases were not required for aminoacylation of tRNA$^{Phe}$. This full-length tRNA$^{Phe}$ transcript was aminoacylated at a rate comparable to that of the native tRNA, and had nearly the same temperature stability as the native tRNA.

A series of transplantation experiments utilizing full-length transcripts of tRNA$^{Phe}$, yeast tRNA$^{mMet}$, and yeast tRNA$^{Arg}$ was used to narrow the yeast tRNA$^{Phe}$ recognition set to G20, G34, A35, A36, and A7373. These five nucleotides are outside the conserved set of nucleotides for all tRNAs, but fall within single stranded regions where the bases are most exposed. In further studies of the properties of unmodified in vitro transcripts, the structure of yeast tRNA$^{Phe}$ transcript was analyzed by NMR, as reported by Samuelsson, et al., *J. Biol. Chem.* 263, 13692-13699 (1988). Substitutions at G20 do not produce large structural alterations, suggesting that the poor aminoacylation of tRNA$^{Phe}$ variants at this position may arise from the loss of a specific protein-tRNA contact.

The yeast tRNA$^{Phe}$ system is an example whose recognition determinants are distributed in at least three regions of the tRNA structure: the anticodon, the acceptor end (specifically, the discriminator base), and an unpaired base that projects from the surface of the tRNA. This distribution is seemingly in contrast to the recognition of tRNA$^{Met}$. However, it is not clear whether all five of the Phe "determinants" are needed for Phe specificity in vivo. For example, the anticodon alone may be sufficient.

EXAMPLE 2

Determination of tRNA$^{Phe}$ Recognition Features by the Chemical Synthesis of tDNA Substrates Another approach to the tRNA$^{Phe}$ recognition features the chemical synthesis of tDNA substrates. Roe and his coworkers, *Science* 241, 74-79 (1988), synthesized 76-nucleotide DNA oligomers corresponding to the sequences of *E. coli* tRNA$^{Phe}$ and of *E. coli* tRNA$^{Lys}$, made with either ribo or deoxy adenosines at the 3' ends. Aminoacylation of tRNA$^{Phe}$, but not of tDNA$^{Lys}$, was dependent on the presence of riboadenosine at the 3' end, which is consistent with the observation that the 3'-end of *E. coli* tRNA$^{Phe}$ requires a 2' hydroxyl for aminoacylation. Both of these tDNAs could only be aminoacylated to approximately 15% of the theoretical maximum, which may have been due to incomplete de-protection of some of the bases after the synthesis. Optimal aminoacylation for both substrates was obtained at pH 5.5 and in the presence of 20% dimethyl sulfoxide. These conditions are known to promote mis-acylation. Kinetic parameters obtained under these conditions for the tDNAs were within a factor of 10 of the native tRNa.

A possible explanation for these results is that the major determinants for recognition are single stranded regions, as in the case of yeast tRNA$_{Phe}$, where the difference between tDNA and tRNA structure is least. In contract, for substrates where helical regions encode determinants for recognition, the difference between A-form and B-form helices could prevent cross-aminoacylation of tDNA and tRNA substrates.

EXAMPLE 3

Determination of the Recognition Determinants of *E. coli* tRNA$^{Ala}$

A. Whole tRNA Substrates:

The principal recognition determinants of *E. coli* tRNA$^{Ala}$ were first identified by screening nucleotide sequence variants of an amber-suppressing derivative of tRNA$^{Ala}$. Through systematic mutagenesis of the non-conserved positions in tRNA$_{Ala}$, with an emphasis on variations along the inside of the L-shaped structure, Hou and Schimmel, *Nature* 333, 140-145 (1988), determined that G:C and A:U substitutions at G3:U70 uniquely eliminated alanine acceptance. Introduction of G3:U70 into tRNA$_{Cys}$, tRNA$^{Phe}$, and tRNA$^{Tyr}$ conferred alanine acceptance on each tRNA in vivo. Because G3:U70 is unique to tRNA$^{Ala}$ in *E. coli*, the results suggested that tRNA$^{Ala}$ may be discriminated from all of the tRNAs on the basis of this single base pair. In later studies, Hou and Schimmel, *Biochemistry* 28, 6800-6804 (1989), showed that eukaryotic alanine tRNAs from *B. mori* and human, which encode G3:U70, were also functional alanine-inserting suppressors in *E. coli*.

The role of the G3:U70 base pair in alanine tRNA synthetase recognition was also investigated in vitro. It was established that G3:U70 was required for the in vitro alanine acceptance of tRNA$^{Ala}$, and that tRNA$^{Cys}$ and tRNA$^{Tyr}$ became substrates in vitro when G3:U70 was introduced. The G3:U70 tRNA$^{Cys}$ amber suppressor inserts alanine in vivo and no detectable cysteine, but it had a reduced rate and extent of aminoacylation in vitro. In contrast, the G3:U70 tRNA$^{Tyr}$ substrate is efficiently and completely aminoacylated. Alanine tRNA synthetases from the insect *B. mori* and from human cells also demonstrate G3:U70-dependent in vitro aminoacylation of their homologous substrates, suggesting that the role of this base pair has been conserved during evolution.

Park, et al., *Biochemistry* 28, 2740-2746 (1989), showed that the *E. coli* enzyme recognizes the G3:U70 base pair during both the binding and catalytic steps of aminoacylation. In particular, when A3:U70 tRNA$^{Ala}$ is bound to the enzyme at a site which competitively inhibits binding of native tRNA$^{Ala}$, there is no aminoacylation of the A3:U70 species. Thus, the G3:U70 determinant may trigger a conformational change in the transition state of the reaction.

B. Minihelix Substrates.

Independent support for the role of the G3:U70 base pair in the catalytic steps of aminoacylation was provided by the analysis of truncated derivatives of tRNA$^{Ala}$ which can be aminoacylated with alanine. Through the use of the in vitro T7 transcription system, short transcripts corresponding to the 12 bp acceptor-TϕC stem and loop of E. coli alanine tRNA$^{Ala}$ were analyzed for alanine acceptance, as described by Franckly and Schimmel, Nature 337, 478-481 (1989). This segment constitutes one domain or "arm" of the L-shaped tRNA structure (see FIG. 2). In a footprint of whole tRNA$^{Ala}$, alanine tRNA synthetase also protects the acceptor-TϕC region from nuclease attack, but does not protect either the D-stem and loop or the anticodon. This domain is aminoacylated with alanine with a kcat comparable to that of native tRNA; a small elevation of Km corresponds to a loss of interaction energy of only 1 kcal mole$^{-1}$. The smallest substrate tested was a seven base pair helix and five nucleotide loop that are based on the sequence of the acceptor stem. Efficient aminoacylation of this substrate showed that sequences outside of acceptor helix are dispensable for charging. In addition, transplantation of G3:U70 into a minihelix based on the acceptor-TϕC sequences of tRNA$^{Tyr}$ conferred efficient alanine acceptance in vitro. The kinetic parameters for aminoacylation of this substrate are nearly the same as for the aminoacylation of G3:U70 tRNA$^{Tyr}$. Thus, the 49 additional nucleotides of tRNA$^{Tyr}$ do not perturb the interaction of the enzyme with the acceptor helix.

The minihelix system resolved two aspects of tRNA$^{Ala}$ recognition raised by in vivo studies. Weak suppression of amber codons in β-galactosidase mRNA by tRNA$^{Ala}$ variants encoding alternative bases pairs at the 3:70 position was observed. Among these, variants encoding U:G, G,A, A:C, C,A and U,U inserted alanine among other amino acids. Using the minihelix systems, U3,U70 and G3,G70 variants were synthesized and found to be completely inactive for aminoacylation. In similar assays utilizing full length tRNA$^{Ala}$ variants, those encoding U:G, G:C, or A:U base pairs at position 3:70 were also defective for aminocylation.

A further question addressed with the minihelix substrates concerns the effect of transplanting G3:U70 into tRNA$^{Cys}$. In contrast to G3:U70-encoding substrates that are efficiently aminoacylated by alanine tRNA synthetase, tRNA$^{Cys}$ encodes a U at position 73 instead of an A. This nucleotide was originally called the discriminator, because tRNAs specific for amino acids of a particular chemical type (e.g. hydrophobic) had the same base at position 73 (i.e, an A). Using minihelix$^{Ala}$ and minihelix$^{Cys}$ variants with various nucleotide substitutions at position 73, in vitro charging assays revealed that an A at position 73 is required for efficient aminoacylation by purified alanine tRNA synthetase. The substitution of other nucleotides at position 73 sharply decreased the rate and extent of G3:U70 aminocylation in vitro. Thus, G3:U70 alone is sufficient to confer alanine acceptance, but position 73 has a significant modulatory effect.

The idea of "primary" (i.e., G3:U70) and "secondary" (i.e., A73) recognition determinants may be a feature of tRNA recognition. As described earlier, both the arginine CCG anticodon and A20 must be introduced into tRNA$_i^{Met}$ to achieve efficient in vitro aminoacylation with arginine tRNA synthetase. Of these two determinants, the introduction of the CCG anticodon alone into tRNA$^{Met}$ is 40-fold more effective in raising Vmax/Km, as compared to A20 tRNA$^{Met}$. The presence of multiple recognition determinants in a tRNA implies nothing about the degree of interaction between them.

There may be other tRNAs in which the acceptor stem is the primary location for recognition determinants. All sequenced tRNA$^{His}$ molecules contain an additional G at their 5' ends, making them one nucleotide longer than other tRNAs at this end. This additional nucleotide is paired with C73 in E. coli tRNA$^{His}$. Recently, Himeo, et al., Nucl. Acids. Res. 19, 7855-7863 (1989), reported that this G-1:C73 base pair in E. coli tRNA$^{His}$ is required for efficient aminoacylation of synthetic transcripts. All substitutions of this base pair (including a triphosphate variant at the −1 position) had a deleterious effect on aminoacylation, suggesting that the enzyme is sensitive to changes in the tRNA at this position.

EXAMPLE 4

Modification of a Base is Necessary for tRNA$^{Ile}$ Recognition

In the examples discussed above, the high rate and extent of aminoacylation observed with synthetic RNA transcripts suggests that the absence of modified bases has little or no effect on aminoacylation. Muramatsu, et al., Nature 336, 179-181 (1988), recently described an example with tRNA$^{Ile}$ where a modified anticodon base plays a crucial role in synthetase recognition.

There are two E. coli isoleucine tRNA isoacceptors that are substrates for isoleucine tRNA synthetase. The major species (GAU anticodon) reads AUU and AUC codons, while the minor species reads AUA codons through an LAU anticodon. L is the modified base lysidine, which has the ε-amino group of a lysine joined to C2 of the pyrimidine ring of cytidine. Through the use of anticodon replacement techniques, the substitution of CAU for LAU at the tRNA$^{Ile2}$ anticodon was demonstrated to abolish aminoacylation by isoleucine tRNA synthetase. Concomitantly, the tRNA$^{Ile}$ (CAU) became a good substrate for methionine tRNA synthetase. Thus, a G or an L at position 34 specifies isoleucine acceptance in this tRNA. Examination of the two bases suggests that the e-nitrogen of lysine may be a surrogate for N3 of guanine to make a portion of L resemble G.

In vitro RNA synthesis is most useful when combined with a complementary method to rapidly identify positions of potential interest in a given RNA structure. A genetic method such as amber suppression, in which a great number of variants can be rapidly screened, is essential when a priori there is no clear rationale for selecting target nucleotides for mutagenesis. Once a mutant is isolated that is defective for a particular function in vivo, the systematic in vitro synthesis and characterization of RNAs that analytically define the mutant phenotype can be undertaken.

However, there are two instances where such a genetic screen may not be necessary. First, there may be prior evidence, such as molecular phylogeny, that points to a particular region as important for a given function. For example, specific nucleotides in predicted helices can be tested explicitly. Second, the regions of functional importance in a large RNA molecule can sometimes be addressed by synthesis of a series of deletion mutants which are tested in an in vitro assay. This approach is particularly effective when domains can be identified, such as the two which make up the L-shaped tRNA structure. In these cases, transcripts can be made which encode a single domain. This approach offers the ability to study those mutants that might not be easily tested in vivo.

Summary.

The role of nucleic acid conformation in sequence specific recognition can be studied through the use of chemical synthesis. Ribo- and deoxyribonucleotides can be programmed in predetermined blocks in a sequence, resulting in the formation of mixed RNA-DNA molecules. These hybrid molecules could then be used as substrates for in vitro assays, and might allow conclusions to be drawn about the role of minor groove interactions. The aminoacylation of tDNA$^{Phe}$ suggests that not all synthetases require the A-form that is characteristic of RNA helices. As shown in the examples, tRNA recognition nucleotides can be either paired or unpaired. In the case of tRNA$^{Met}$ and tRNA$^{Phe}$, important bases for recognition are located in the anticodon. In these cases, the helical nature of the tRNA would not be predicted to play an important role in the presentation of the bases to the protein. Such tRNAs are candidates for studies of the tDNA analogue of a tRNA. In tRNA$^{Ala}$, the G3:U70 base pair is located within a helical region of the tRNA, so that the corresponding DNA analogue might be inactive.

Other protein-tRNA systems can be addressed through the use of in vitro RNA synthesis. These include the CCA nucleotidyl transferase and other tRNA modification enzymes, elongation factor Tu, and initiation factors. For example, Seong and Rajbhandary, *J. Biol. Chem.* 246, 6504-6508 (1989), have used an in vivo system to show that elongator tRNA$^{Met}$ and initiator tRNA$_i^{Met}$ are distinguished by initiation factors on the basis of a single base pair mismatch at the 5' end of the initiator tRNA.

The interpretation of experiments on systems other than tRNAs, such as the M1 RNA of RNase P, are hampered by the lack of three dimensional structural information. The tRNA structure was possible in part because of the availability of relatively large quantities of a specific tRNA, such as tRNA$^{Phe}$, from a convenient natural source (i.e. baker's yeast). RNA synthesis has developed sufficiently that it can now make available large amounts of otherwise scarce RNA species, such that structural analysis of these molecules is now feasible. Thus, while the first experiments exploited the use of RNA synthesis to generate sequence variants which define determinants for recognition in a defined structure (i.e., transfer RNA), synthesis can now be used as the means to generate the materials themselves that will be used for structure determinations. RNA studies in this matter could include defined elements or domains of M1 RNA, ribosomal RNAs, and cellular and viral RNAs.

Computer Modeling.

Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

An example of the molecular modelling system described generally above consists of the CHARMm and QUANTA programs, Polygen Corporation, Waltham, Mass. CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Ripka, *New Scientist* 54-57 (Jun. 16, 1988) who states, "The linear sequence of amino acids in the protein has the interesting property that it uniquely determines how [the] chain will fold. The sequence, therefore, controls both the protein's three-dimensional structure and ultimately its function, which depends largely on the protein's shape . . . Knowing what this three-dimensional structure looks like is crucial to the process of designing drugs . . . Two spectroscopic techniques help to determine the complex 3-D structures of proteins. The first is X-ray crystallography . . . A second, and relatively new technique, uses nuclear magnetic resonance (NMR) to detect which atoms of the protein are brought close together by the folding process. By combining these analytical data with building models, we can arrive at a 3-D structure for the protein . . . [Another idea] is to use the 3-D structures already determined by X-ray crystallography and try to develop rules based on how these proteins fold . . . To generate [a computer] graphics display, we feed the coordinates or positions of the atoms of the protein structure produced by X-ray, NMR or model building into [a graphics] computer program. At this juncture, the medicinal chemist and molecular modelers are at last ready to begin the process of drug design by computer . . . The first and most obvious [factor to consider] is that the small molecule must have a geometrically complementary shape to the enzyme's active site (the key must have an appropriate shape to fit the lock). In addition, it must consist of appropriate atoms so that the electronic characteristics of the molecule complements those of the atoms making up the walls of the active site. In other words, positively charged, polarised, groups of atoms in the small molecule must fit negatively charged groups in the site, not positively charged groups, which would repel each other. We are just beginning to understand the rules governing the relative importance of specific interactions. Finally, the compound must be stable (stay around long enough to bind to the protein) and relatively easy to synthesize to be a viable proposition."; McKinaly and Rossmann, *Annu. Rev. Pharmacol. Toxiciol.* 29, 111-122 (1989) who state, "Rational [antiviral] drug design, defined as the directed synthesis of new compounds based on an understanding of a prototype drug/viral structural or functional protein interaction at the atomic level, is only now becoming a viable alternative to empirical screening . . . The most important ingredient in a drug design program is the obvious need to predict the activity of a molecule before the effort is invested to synthesize it. While a certain amount of success can be had by viewing a ligand/protein structure on a graphics terminal, the multiplicity of possible conformations the ligand and protein can assume make it exceedingly difficult to make accurate predictions with any regularity. Recent developments in the use of thermodynamic calculations and molecular dynamics simulations permit consideration of previously impossible computational problems through the use of supercomputers and new computational approaches. The thermodynamic-cyclic perturbation approach to thermodynamic calculations is likely to be increasingly used in the future (McCammon, J. A. 1987, Computer-aided molecular design. *Science* 238:486-91.) Since the free energy change of binding of a drug to a protein or virus would be exceedingly difficult, if not impossible, to calculate, this method enables one to calculate the relative free energy change for the binding of two different compounds. These calculations will enable the researcher to predict whether a compound proposed for synthesis is likely to possess a greater binding affinity to the target. The second promising application of computational chemistry to drug design is molecular dynamics simulation (McCammon, J. A., Harvey, S. C. 1987, *Dynamics of Proteins and Nucleic Acids*. Cambridge, London, New York: Cambridge Univ. Press, pp. 234). The object of this exercise is to simulate the dynamics of the drug/protein interactions based on the dynamical trajectories of each atom. This type of analysis can help identify areas of the drug where considerable movement is occurring when bound to the target, suggesting that the conformation of the drug may need to be constrained to maximize activity. This analysis may also suggest ways in which the drug is exerting its effect on the protein."; Perry and Davies, *OSAR: Quantitative Structure-Activity Relationships in Drug Design* pp. 189-193 (Alan R. Liss, Inc. 1989) who state, "Chemstat has been developed to allow the rapid construction of a database containing molecular coordinates together with computed and experimental parameters and biological data . . . The database is stored on disk and comprises a number of segments. Each segment is a molecular structure together with associated information stored in 104 data fields. Some or all of the segments may be read into the Chem-X data matrix where information may be added, deleted or modified. Data may be placed in the fields by calculating properties within Chem-X (or interfaced programs) or by reading from an external file. Each property to be calculated must first be defined in terms of a ChemStat template file. This flexible method allows definitions from the supplied 'library' of calculation types, user-supplied Chem-X command files or external programs interfaced through ChemLib. An automatic procedure is then invoked whereby each property is calculated for each segment before the database is updated. This will generally result in a data matrix containing a vast amount of information which must be 'sifted' before it can be used predicatively. Key fields must be identified as being associated with the required property. A novel method of data reduction is employed by ChemStat to address this problem. One field in the data matrix is specified as being the 'observed' field (generally the biological activity). By the automatic calculation of the appropriate correlation coefficients, those fields which correlate best with this field but are not highly inter-correlated can be listed and passed to the reduced data matrix. The data may be viewed graphically or in tabular form and fields and segments may be interactively included or excluded from the calculations. More sophisticated statistical techniques such as principal component analysis or pattern recognition are made available through an interface to some of the more popular commercial packages. Data from the reduced data matrix is passed to the program and new or modified data can be passed back to Chem-X via an intermediate file. Once the key fields have been identified, they can be used as predictor variables for multiple regression against the 'observed' field. ChemStat will determine the regression equation and calculate predicted values for the 'observed' variable from the values of the predictor variables for each segment . . . ChemStat, ChemLib and ChemQH are modules of the molecular modelling software Chem-X, developed and distributed by Chemical Design Limited, Oxford, England"; Lewis and Dean, *Proc. R. Soc. Lond.* 236, 125-140 and 141-162 (1989) who state, "This paper examines the problem of automated structure generation at specified binding sites. The objective is to obtain molecular graphs that span the binding site and incorporate predicted ligand points at their vertices. Three approaches are considered: brute force techniques, subgraph addition and spacer skeletons. A spacer skeletons is a device for representing several distinct classes of compound within just one structure. It is used to reduce the amount of searching that must be done in the primary phase of structure generation . . . The CDS [Cambridge Structural Database] can be searched to find all the compounds that contain a certain molecular fragment and the geometric parameters of this fragment in each compound can be calculated. Certain geometric calculations can be performed directly on the DATA file at the retrieval stage and the redundant information on irrelevant parts of the molecule is ignored. The GEOM program will compute angles, centroids, vectors, planes and internal coordinates for a user-specified fragment (Allen et al. 1979 [*Acta crystallogr*. B 35,2331-2339]). This powerful facility can provide the user with a comprehensive range of geometric parameters, which can then be analysed statistically. This database is of great use in the building of spacer skeletons designed to model many different fragments . . . The results of each search through the database were read into a geometric analysis program which retrieved the coordinate data from the DATA file, plotted out the whole molecule by using the PLUTO 78 package (Motherwell & Clegg 1978 [PLUTO78. Program for plotting molecular and crystal structures. In *Cambridge crystallographic files*. University of Manchester Regional Computer Centre.]) and calculated the least-squares plane through the atoms in the fragments. The deviation of each atom from the plane was computed together with the distance from the atom to the centroid of the fragment. The results were plotted as frequency histograms of (i) the root mean square deviation and (ii) the distance of highly deviant atoms from the centroid . . . The program MNET was written to provide a reliable means of constructing spacer skeletons either round a starting nucleus or from scratch."; and, with respect to a model receptor for nucleic acid components, Askew, et al., *J. Am. Chem. Soc.* 111, 1082-1090 (1989) who state, "The most relevant precedent for base pairing in model systems is that of Rich, [Kyogoku et al., *J. Am. Chem. Soc.* 1968, 90,4151-4157,] using cyclohexyluracil binding to 9-ethyladenine in $CHCl_3$. Systematic structural modifications in both components were made in this study and revealed trends concerning steric effects and acid-base effects. At the same time these systems were used to examiner the kinetics of the base-pairing event. Aromatic stacking interactions of simple bases were studied by Chan [Chan et al., *Am. Chem. Soc.* 1964, 86, 4182. Schweitzer et al. Ibid. 1965, 87, 5241-5247. Iwahashi et al. Ibid. 1977, 99, 7761-7765.] in aqueous solutions, whereas Tinoco et al. [Tinoco et al., *Nature, New Biol.* 1973, 246, 40-41] have developed a set of rules for the sequence-specific hydrogen bonding and stacking contributions of various base pairs to the stability of intact nucleic acids. Our departure from previous model studies is made possible by the construction of a new molecular shape which permits both hydrogen bonding and aromatic stacking forces to act simultaneously. The structural developments are a consequence of the use of Kemp's [Kemp et al., J. Org. Chem. 1981, 46, 5140-5143] triacid 3, in which a U-shaped (diaxial) relationship exists between any two carboxyl functions. Conversion of the triacid to the imide acid chloride 4b gives an acylating agent that can be attached via amide or ester linkages to practically any available aromatic surface. The resulting structure features an aromatic plane which can be roughly parallel to that of the atoms in the imide function; hydrogen bonding and stacking forces converge from perpendicular directions to provide a microenvironment complimentary to adenine derivatives. The same structural features are also present in a model for thymine and uracil recognition developed by Hamilton [Hamilton et al., *J. Am. Chem. Soc.* 1987, 109, 5035-5036.]".

Computer modelling has found limited use in the design of compounds that will interact with nucleic acids, because the generation of force field data and x-ray crystallographic information has lagged behind computer technology. CHARMm has been used for visualization of the three-dimensional structure of parts of four RNAs, as reported by Mei, et al., *Proc. Natl. Acad. Sci.* 86:9727 (1989), but computer modelling has not been used to design compounds that will bind to and inactivate RNA.

Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of drugs specific to regions of RNA, once that region is identified. Synthesis of RNA-specific compounds.

Compounds which specifically inhibit the function of the targeted RNA are synthesized using methods known to those skilled in the art based on the sequence and structure determined as described above. Known compounds can also be modified or selected on the basis of their existing structure, once the requirements for specificity are known.

The compounds can be organic, inorganic, proteins, or even other nucleic acids. Specific binding to the targeted molecule can be achieved by including in the molecule complementary nucleic acid sequence that forms base pairs with the targeted RNA under appropriate conditions, or by inclusion of chemical groups having the correct spatial location and charge.

In the preferred embodiments, compounds are designed as a peptide or organic compound with hydrogen bond donor and acceptor sites arranged to be complementary to the RNA.

For peptides, the proposed hydrogen acceptors are the carbonyl oxygens of the peptide backbone; the side chains of glutamic acid, aspartic acid, asparagine, glutamine; and the imidazole nitrogen of histidine. The proposed hydrogen bond donors are the backbone amides N—H; the side chain hydroxyl groups of serine, threonine, and tyrosine; the sulfhydryl of cysteine; the indole of N—H of tryptophan; the guanidino group of arginine; the $NH_2$ of glutamine and asparagine; and the N—H of imidazole side chain of histidine.

A peptide is formed with the amino acids ordered to yield the correct spatial arrangement of hydrogen bond acceptors and donors, when the peptide is in a specific conformation induced and stabilized by binding to the target RNA segment). The likelihood of forming the desired conformation can be refined and/or optimized using molecular computational programs.

Organic compounds can be designed to be rigid, or to present hydrogen bonding groups on edge or plane, which can interact with complementary sites. Rebek, *Science* 235, 1478-1484 (1987) and Rebek, et al., *J. Am. Chem. Soc.* 109, 2426-2431 (1987), have summarized some of these approaches and the mechanisms involved in binding of compounds to regions of proteins.

Synthetic methods can be used by one skilled in the art to make compounds that interact with functional groups in the minor groove of RNA.

In some cases, the inhibitory compound is a nucleic acid molecule, either RNA or DNA. This can be prepared synthetically using commercially available equipment or by cloning of an appropriate sequence which is designed or derived from the sequence to be inhibited.

The methods, reagents, and computer software programs described in the references cited herein and other methods and materials useful for molecular modeling and chemical synthesis are known to those skilled in the art.

Delivery of the Compounds to the Targeted Ribonucleic Acid.

As discussed above, any RNA that is important in a disease process can be targeted and an appropriate inhibitory compound made synthetically or by copying cloned sequence. The RNA to be inhibited will usually be in the cytoplasm or in the nucleus. Important examples of the viral agents that replicate in the cell nucleus include herpesviruses (including herpes simplex virus, varicella-herpes zoster virus, cytomegalovirus, and Epstein-Barr virus), adenoviruses, paramyxoviruses such as measles, and the retroviruses, such as human immunodeficiency virus (HIV I, HIV II and HIV III). Other nucleic acids that are located in the nucleus, for example, oncogenes that are integrated in the host chromosome, can be inhibited in the nucleus or in the cytoplasm, after they have been transcribed into mRNA. A number of other pathogenic agents are present only in the cytoplasm of the infected cells.

Systemically or Topically Administered Compositions.

The inhibitory compound can be administered topically or systemically in a suitable pharmaceutical carrier. *Remington's Pharmaceutical Sciences,* 15th Edition by E. W. Martin (Mark Publishing Company, 1975), the teachings of which are incorporated herein by reference, discloses typical carriers and methods of preparation. The inhibitory compound may also be encapsulated in suitable biocompatible microcapsules or liposomes for targeting to phagocytic cells. Such systems are well known to those skilled in the art.

Therapeutically the compounds are administered as a pharmaceutical composition consisting of an effective amount of the compound to inhibit transcription and/or translation, or function, of a targeted RNA and a pharmaceutically acceptable carrier. Examples of typical pharmaceutical carriers, used alone or in combination, include one or more solid, semi-solid, or liquid diluents, fillers and formulation adjuvants which are non-toxic, inert and pharmaceutically acceptable. Such pharmaceutical compositions are preferable in dosage unit form, i.e., physically discreet units containing a predetermined amount of the drug corresponding to a fraction or multiple of the dose which is calculated to produce the desired therapeutic response, conventionally prepared as tablets, lozenges, capsules, powders, aqueous or oily suspensions, syrups, elixirs, and aqueous solutions. Oral compositions are in the form of tablets or capsules and may contain conventional excipients such as binding agents, (e.g., syrup, acacia, gelatin, sorbitol, tragacanth or polyvinylpyrrolidone), fillers (e.g., lactose, sugar, corn starch, calcium phosphate, sorbitol, or glycine), lubricants (e.g., magnesium stearate, talc, polyethylene glycol or silica), disintegrants (e.g., starch) and wetting agents (e.g., sodium lauryl sulfate). Solutions or suspensions of the inhibitory compound with conventional pharmaceutical vehicles are employed for parenteral compositions, such as an aqueous solution for intravenous injection or an oily suspension for intramuscular injection.

Vector-Mediated Delivery of Inhibitory Nucleic Acid Compound.

Preferred vectors are viral vectors such as the retroviruses which introduce the inhibitory nucleic acid directly into the nucleus. Defective retroviral vectors, which incorporate their own RNA sequence in the form of DNA into the host chromosome, can be engineered to incorporate the inhibitory RNA into the host, where copies will be made and released into the cytoplasm to interact with the target nucleotide sequences.

Compositions for Systemic Administration of the Inhibitory Compounds.

For clinical applications, the dosage and the dosage regimen in each case should be carefully adjusted, utilizing sound professional judgment and consideration of the age, weight and condition of the recipient, the root of administration and the nature and gravity of the illness.

The present invention will be further understood by reference to the following non-limiting examples.

EXAMPLE 5

Targeting of RNA-Specific Compounds to Inactivate Viral-Specific RNA

The methods described above for determining the sequence and structure of the RNA that is critical for activity in combination with specific to the RNA to be inhibited can be applied to the selective inhibition of RNA of human immunodeficiency viral (HIV) or other viral origin.

Methods similar to those applied above to tRNAs are applied to the RNA molecules associated with retroviruses such as HIV-1, 2, 3. Important RNA sequences in these molecules have already been identified and can be targeted (see, for example, *The Science of AIDS*, Readings from Scientific American Magazine (W.H. Freeman and Co., New York, 1988 and 1989), especially pages 63-110).

Target sequences are the small RNA segment in the rev response element of HIV-1 which is essential for biological activity, as described by Malim, et al., *Cell* 60,675-683 (1990); the small segment of RNA of Rous sarcoma virus which is necessary for production of specific viral polypeptides, as described by Jacks, et al., *Cell* 55, 447-458 (1988); the RNA element of non-retroviral avian coronavirus infectious bronchitis virus, as described by Brierley, et al., *Cell* 57, 537-547 (1989).

The method for identifying the critical nucleotides and associated structure in these RNA sequences is summarized as follows:

1. in vitro RNA synthesis or in vivo synthesis in an appropriate host where the desired RNA is expressed from a recombinant cDNA clone (Hou & Schimmel 1988).
2. identification of positions of potential interest in a given RNA structure:
    (a) When no rationale for selecting target nucleotides for mutagenesis exists, mutants are made and rapidly screened for absence (or presence) of a specific function, for example, amber suppression or aminoacylation. Once a mutant that is defective for a function (e.g. recognition of synthetase) is identified, the associated RNAs are synthesized and characterized to define the active sites.
    (b) When it is believed that a particular region has a given function, this is tested explicitly, by altering specific nucleotides in the RNA helices or making deletion mutants, which are tested in an in vivo or in vitro assay. This is particularly appropriate when domains such as the two that make up the L-shaped tRNA structure can be identified.

The role of conformation in sequence-specific recognition is determined by:

1. Program by chemical synthesis RNA-DNA hybrid molecule, consisting of predetermined blocks of a sequence. Do in vitro assays to determine role of minor groove.
2. Design compounds with computer. All computational analyses and graphics can be carried out, for example, on a Silicon Graphics Iris workstation, using CHARMm and QUANTA (versions 3.0) programs (Polygen Corporation).
3. Synthesize compounds.
4. Screen biochemically for specific interactions between RNA and compounds.

There have been a number of studies on the binding of small molecules to nucleic acids, for example, by Rebek, et al., *J. Am. Chem. Soc.* 109(16), 5033-5035 (1987), Jeong and Rebek, *J. Am. Chem. Soc.* 110(10), 3327-3328 (1988), and Askew, et al., *J. Am. Chem. Soc.* 111(3), 1082-1090 (1989), that summarize the studies using individual portions of these methods, applied to design of drugs targeted to specific proteins.

The drugs that bind to specific sequences take advantage of the pattern of hydrogen bonded donor and acceptor sites that are in the minor groove (see FIG. 3). Specifically, hydrogen bonded donors are matched with acceptors according to the particular sequence that is targeted. Hydrogen bond acceptors on the drug molecules could include carbonyl oxygens (C=O) and conjugated nitrogen atoms (—N=), among other possibilities, and donors would include -NH$_2$, —NH—, and —OH groups. These groups should be spaced to match exactly the spacing of the complementary groups on the nucleic acid sequence that is the target site.

EXAMPLE 6

Design of Compounds Specifically Inhibiting Eukaryotic Protein Synthesis by Interaction with Bacterial tRNA Molecules but not Eukaryotic tRNA The methods described above, in combination with the information presently known about tRNA molecules in procaryotic cells and in eukaryotic cells, can be applied to the design of small molecules that bind to specific RNAs that are essential for cell viability. For example, a drug that binds selectively to the G3:U70 base pair of tRNA$^{Ala}$ could arrest protein synthesis. By taking advantage of sequence differences around G3:U70 between the human tRNA$^{Ala}$ and that of a pathogenic organism, selective drug binding can be achieved.

Figure 4A:
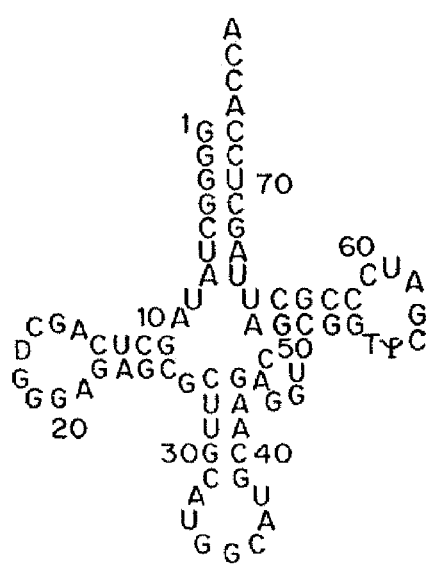
FIGS. 4A and 4B are the respective alanine tRNA for *E. coli* (FIG. 4A) and humans (FIG. 4B).
Figure 4B:
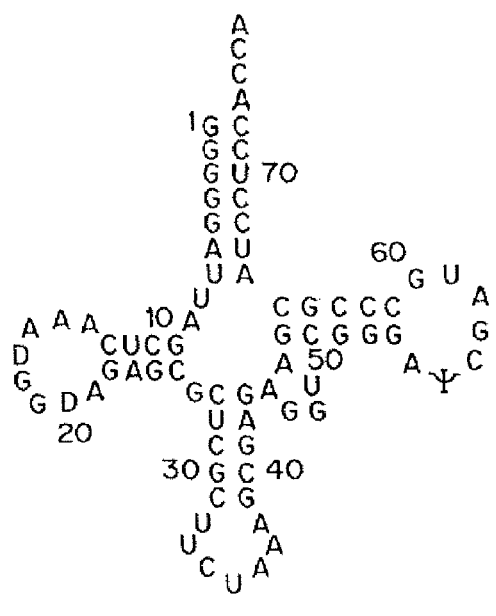

FIG. 4 compares the sequences of an *E. coli* and a cytoplasmic human alanine tRNA. The shaded nucleotides are those that distinguish the human from the *E. coli* tRNA. Thus, three base pairs that are proximate to the critical G3:U70 recognition site are among those that distinguish the human from the *E. coli* tRNA. A drug that binds to the G3:U70 base pair and to the three proximal pairs that distinguishes the *E. coli* from the human tRNA would selectively inactivate the bacterial species and arrest protein synthesis. The unique pattern of hydrogen bond acceptors and donors on the target sequence is determined by FIG. 3, and the complementary pattern will be built into the drug. Based on the spacing of the base pairs and of the hydrogen bond acceptor and donor groups, this drug would have a size of 12-18 angstroms.

EXAMPLE 7

Design of Molecules Specifically Inhibiting RNA-Dependent Reverse Transcriptase of Retroviruses The interaction between the RNA-dependent reverse transcriptase of retroviruses and the specific tRNA that acts as a primer for reverse transcriptase is another system that can be used as the basis for the design of drugs that bind to RNA. The annealing of the primer tRNA to the primer binding site is the first step in initiation of cDNA synthesis by reverse transcriptase, and thus represents a potential target for the arrest of viral multiplication.

As described by Varmus, *Science* 216:812 (1982), HIV reverse transcriptase and primer lysine tRNA form a complex that can be detected by glycerol gradient centrifugation. This can serve as an assay for testing inhibitors of the binding reaction. The synthesis of RNA length and sequence variants could be used in this system to define determinants on the tRNA required for binding and serve as initial targets for drug design. The reverse transcriptase binds to the anticodon loop of the tRNA. A drug designed to be specific for the tRNA and block binding will arrest replication of the virus by the host cell. See also Bordier, et al., *Nucleic Acids Research* 18, 429-436 (1990).

The targeting of $tRNA^{Lys}$ to block HIV reverse transcriptase would follow considerations similar to those described for the design of a drug that binds $tRNA^{Ala}$. The site of binding of the tRNA to the viral RNA (primer bonding site), could also be a target for a drug.

EXAMPLE 8

Design of Compounds Selectively Inhibiting rRNA for Use as a Chemotherapeutic Agent α-sarcin is a cytotoxic protein with potent antisarcoma activity, isolated from a mold, that inactivates ribosomes by cleaving the rRNA. Endo, et al., *J. Biol. Chem.* 265:2216 (1990) determined that its target site is one phosphodiester bond on the 3' side of G-4325 in a loop at the 3' end of eukaryotic 28 S rRNA. The cleavage site is within a highly-conserved, 14-nucleotide segment. This segment is nearly universal in all rRNAs. Cleavage inactivates the ribosomes of all organisms that have been tested, implying that the rRNA sequence is crucial for function. Treatment of ribosomes with other ribonucleases causes extensive digestion of rRNA.

Endo, et al. produced a synthetic nucleotide with the appropriate sequence and secondary structure by using a synthetic DNA template and phage T7 RNA polymerase, and determined that the active site for binding between the rRNA and the α-sarcin is a G base at 4325 plus a minimum of three base pairs in the helical stem. The base pairs modify recognition but are not absolutely necessary. The flanking base pairs around G-4325 are important; alteration blocks cleavage by the α-sarcin. Endo, et al., proposed that the α-sarcin domain RNA participates in elongation factor catalyzed binding of aminoacyl-tRNA and of translocation; that translocation is driven by transitions in the structure of the α-sarcin domain RNA initiated by the binding of the factors, or the hydrolysis of GTP, or both; and that the toxin inactivates the ribosomes by preventing this transition.

Alpha-sarcin is too toxic for use clinically to treat tumors, since it binds and cleaves all rRNAs and is highly toxic to normal cells as well as tumor cells. However, because the cleavage site for alpha-sarcin in 28 rRNA is in a region essential for translation, a drug can be designed that is specific to that site and which distinguishes the mammalian sequence from that of an infectious agent. For example, the sequence at the alpha-sarcin cleavage site in the *E. coli* counterpart to mammalian (rat) 28S rRNA is . . . GG<u>C</u>UGCUC<u>C</u>UAGUACGAGAGGA<u>C</u>CGGAGUG GACG . . . , where the bold face G denotes the site of alpha-sarcin cleavage and the nucleotides different from those in the analogous position of the mammalian (rat) 28 S rRNA are indicated by underlines. Many of the nucleotides that are in the region that distinguishes the bacterial from the mammalian species are believed to form an RNA helical secondary structure (Endo et al. 1990). Thus, these base pairs can be targeted, including or not including the cleavage site itself, by a drug that is designed to be complementary to the specific pattern of hydrogen bonded acceptors and donors, as described above for the case of drugs that bind to a bacterial alanine tRNA.

Modifications and variations of the present invention will be obvious to those skilled in the art from the foregoing detailed description. Such modifications and variations are intended to come within the scope of the appended claims.

What is claimed is:

1. A method for designing a compound specifically inhibiting targeted ribonucleic acid function comprising the steps of:
   (a) determining the nucleotide sequence in the targeted ribonucleic acid that is critical to function;
   (b) determining the secondary structure of the region of the targeted ribonucleic acid in which the critical site is located;
   (c) determining the three-dimensional stature of the targeted RNA, including the position of the critical site relative to the major and minor grooves;
   (d) determining the sequence of nucleotides and structure flanking the critical site in the targeted ribonucleic acid that is specific to the critical region of the ribonucleic acid to be inhibited and within the minor groove; and
   (e) synthesizing a compound that will bind specifically to the critical site within the minor groove of the targeted ribonucleic acid thereby inhibiting targeted ribonucleic acid function.

2. The method of claim 1 wherein the ribonucleic acid is selected from the group consisting of mRNA, rRNA, tRNA and viral RNA.

3. The method of claim 1 wherein inhibition of targeted ribonucleic acid function inhibits protein synthesis.

4. The method of claim 3 wherein protein synthesis is inhibited in cells selected from the group consisting of tumor cells, virally infected cells, and bacterial cells.

5. The method of claim 1 wherein the three-dimensional structure is modeled using sequences of the RNA and calculating the minimum energies for these structures.

6. The method of claim 1 wherein the critical region of the targeted ribonucleic acid is determined by mutation of regions of the targeted RNA and comparison of the function of the mutated RNA with the original RNA, wherein mutations that result in mutant RNA having altered function indicate that the site of mutation is a critical site.

7. The method of claim 1 wherein the targeted RNA is a tRNA, wherein the critical region of the tRNA is determined by site directed mutation of the tRNA and analysis of the function of the mutated tRNA.

8. The method of claim 1 further comprising determining an effective amount of the compound and combining the compound with a pharmaceutical carrier.

9. The method of claim 8 wherein the carrier is selected from the group consisting of pharmaceutically acceptable compositions for topical administration, pharmaceutically acceptable compositions for parenteral administration, pharmaceutically acceptable compositions for enteral administration, and combinations thereof.

10. The method of claim 2 wherein the critical site is in the minor groove of the acceptor stem of a tRNA molecule.

11. The method of claim 10 wherein the tRNA molecule is tRNA$^{Ala}$.

12. The method of claim 11 wherein the critical site is the G3:U70 base pair.

13. The method of claim 1 wherein the compound is a nucleic acid and the compound is synthesized in vivo from a retroviral vector.

* * * * *